United States Patent
Jiang et al.

(10) Patent No.: US 12,005,223 B2
(45) Date of Patent: Jun. 11, 2024

(54) DISINFECTION CAP

(71) Applicant: Becton, Dickinson and Company, Franklin Lakes, NJ (US)

(72) Inventors: Chang Jiang, Butler, NJ (US); Amir Harandi, Bloomingdale, NJ (US); Paul P. Marici, Piscataway, NJ (US); Jiayu Liu, Bloomingdale, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 429 days.

(21) Appl. No.: 17/229,166

(22) Filed: Apr. 13, 2021

(65) Prior Publication Data
US 2021/0322752 A1  Oct. 21, 2021

Related U.S. Application Data

(60) Provisional application No. 63/011,357, filed on Apr. 17, 2020.

(51) Int. Cl.
*A61M 39/20* (2006.01)
*A61M 39/16* (2006.01)

(52) U.S. Cl.
CPC ............ *A61M 39/20* (2013.01); *A61M 39/16* (2013.01)

(58) Field of Classification Search
CPC ............................. A61M 39/20; A61M 39/16
See application file for complete search history.

(56) References Cited

U.S. PATENT DOCUMENTS

| | | |
|---|---|---|
| 3,403,679 A | 10/1968 | Sinclair et al. |
| 4,597,758 A | 7/1986 | Aalto et al. |
| 4,642,102 A | 2/1987 | Ohmori |
| 4,711,363 A | 12/1987 | Marino |
| 4,738,376 A | 4/1988 | Markus |
| 4,906,231 A | 3/1990 | Young |
| 5,084,017 A | 1/1992 | Maffetone |
| 5,496,288 A | 3/1996 | Sweeney |
| 5,676,406 A | 10/1997 | Simmons et al. |
| 5,755,696 A | 5/1998 | Caizza |
| 5,984,123 A | 11/1999 | Mogami et al. |

(Continued)

FOREIGN PATENT DOCUMENTS

| | | |
|---|---|---|
| CA | 2523133 C | 2/2013 |
| CN | 1322119 A | 11/2001 |

(Continued)

OTHER PUBLICATIONS

"PCT International Search Report and Written Opinion in PCT/US2021/027219 dated Oct. 22, 2021, 22 pages".

(Continued)

*Primary Examiner* — Bradley J Osinski
(74) *Attorney, Agent, or Firm* — Servilla Whitney LLC

(57) ABSTRACT

A disinfection cap is described for connection to a medical connector; the disinfection cap includes a housing having a top wall and sidewall forming a cavity. In one or more embodiments, a retention rod forming a fluid reservoir is disposed within the cavity for retaining disinfectant. In one or more embodiments, a corrugated capsule is disposed within the cavity for retaining disinfectant. Pressure buildup within the cavity due to insertion of a luer connector causes expulsion of disinfectant, thereby disinfecting the luer connector.

13 Claims, 16 Drawing Sheets

(56) References Cited

U.S. PATENT DOCUMENTS

| | | |
|---|---|---|
| 6,565,529 B1 | 5/2003 | Kimber et al. |
| 6,632,199 B1 | 10/2003 | Tucker et al. |
| 7,083,605 B2 | 8/2006 | Miyahara |
| 8,012,131 B2 | 9/2011 | Moser et al. |
| 8,388,894 B2 | 3/2013 | Colantonio |
| 8,647,308 B2 | 2/2014 | Solomon et al. |
| 8,715,231 B2 | 5/2014 | Woehr |
| 8,721,627 B2 | 5/2014 | Alpert et al. |
| 8,777,504 B2 | 7/2014 | Shaw et al. |
| 8,961,475 B2 | 2/2015 | Solomon et al. |
| 9,039,989 B2 | 3/2015 | Lui et al. |
| 9,132,223 B1 | 9/2015 | Wakeel |
| 9,192,449 B2 | 11/2015 | Kerr et al. |
| 9,867,975 B2 | 1/2018 | Gardner et al. |
| 10,099,048 B2 | 10/2018 | Chiu et al. |
| 10,166,381 B2 | 1/2019 | Gardner et al. |
| 10,376,686 B2 * | 8/2019 | Burkholz ............ A61M 39/162 |
| 10,589,080 B2 | 3/2020 | Hitchcock et al. |
| 10,603,481 B2 | 3/2020 | Avula et al. |
| 10,871,246 B2 | 12/2020 | Marici et al. |
| 11,353,147 B2 | 6/2022 | Marici |
| 11,511,100 B2 | 11/2022 | Ryan |
| 11,628,288 B1 | 4/2023 | Solomon et al. |
| 2003/0093009 A1 | 5/2003 | Newby et al. |
| 2003/0209681 A1 | 11/2003 | Leinsing et al. |
| 2004/0039341 A1 | 2/2004 | Ranalletta |
| 2004/0044318 A1 | 3/2004 | Fiser et al. |
| 2005/0147525 A1 | 7/2005 | Bousquet |
| 2005/0197646 A1 | 9/2005 | Connell et al. |
| 2007/0060904 A1 | 3/2007 | Vedrine et al. |
| 2008/0010766 A1 | 1/2008 | Kaufman et al. |
| 2008/0171995 A1 | 7/2008 | Vitullo et al. |
| 2008/0177250 A1 | 7/2008 | Howlett et al. |
| 2010/0000040 A1 | 1/2010 | Shaw et al. |
| 2010/0049170 A1 | 2/2010 | Solomon et al. |
| 2010/0050351 A1 | 3/2010 | Colantonio et al. |
| 2010/0100056 A1 | 4/2010 | Cawthon et al. |
| 2011/0046603 A1 | 2/2011 | Felsovalyi et al. |
| 2011/0054440 A1 | 3/2011 | Lewis |
| 2011/0213341 A1 | 9/2011 | Solomon et al. |
| 2011/0264037 A1 | 10/2011 | Foshee et al. |
| 2012/0039764 A1 | 2/2012 | Solomon et al. |
| 2012/0111368 A1 | 5/2012 | Rahimy et al. |
| 2012/0123386 A1 | 5/2012 | Tsals |
| 2012/0302997 A1 | 11/2012 | Gardner et al. |
| 2013/0085474 A1 | 4/2013 | Charles et al. |
| 2013/0171030 A1 | 7/2013 | Ferlic et al. |
| 2013/0197485 A1 | 8/2013 | Gardner et al. |
| 2013/0338644 A1 | 12/2013 | Solomon et al. |
| 2014/0052074 A1 | 2/2014 | Tekeste |
| 2014/0150832 A1 | 6/2014 | Rogers et al. |
| 2015/0094666 A1 | 4/2015 | Bates et al. |
| 2016/0045629 A1 | 2/2016 | Gardner et al. |
| 2016/0067422 A1 | 3/2016 | Davis et al. |
| 2016/0158520 A1 | 6/2016 | Ma et al. |
| 2017/0203087 A1 | 7/2017 | Ryan et al. |
| 2018/0085568 A1 | 3/2018 | Drmanovic |
| 2018/0200145 A1 | 7/2018 | Sanders et al. |
| 2018/0200500 A1 | 7/2018 | Ziebol et al. |
| 2018/0237190 A1 | 8/2018 | Iwasaki |
| 2018/0243547 A1 | 8/2018 | Fox et al. |
| 2018/0256879 A1 | 9/2018 | Chiu et al. |
| 2018/0256883 A1 | 9/2018 | Follman et al. |
| 2019/0111245 A1 | 4/2019 | Gardner et al. |
| 2019/0151643 A1 | 5/2019 | Alpert |
| 2019/0234540 A1 | 8/2019 | Marici et al. |
| 2019/0308006 A1 | 10/2019 | Erekovcanski et al. |
| 2019/0351212 A1 | 11/2019 | Dudar et al. |
| 2020/0238070 A1 | 7/2020 | Ryan |
| 2021/0100996 A1 | 4/2021 | Wijesuriya et al. |
| 2021/0187267 A1 | 6/2021 | Jiang |
| 2022/0273931 A1 | 9/2022 | Jiang et al. |
| 2023/0080687 A1 | 3/2023 | Ryan |

FOREIGN PATENT DOCUMENTS

| | | |
|---|---|---|
| CN | 101631585 A | 1/2010 |
| CN | 101980746 A | 2/2011 |
| CN | 201807018 U | 4/2011 |
| CN | 102188766 A | 9/2011 |
| CN | 102448502 A | 5/2012 |
| CN | 103025374 A | 4/2013 |
| CN | 103083767 A | 5/2013 |
| CN | 204161736 U | 2/2015 |
| CN | 206198472 U | 5/2017 |
| DE | 20017013 U1 | 12/2000 |
| DE | 10247963 A1 | 5/2004 |
| DE | 202005004079 U1 | 7/2006 |
| EP | 0589379 A1 | 3/1994 |
| EP | 2832391 A1 | 2/2015 |
| EP | 3275490 A1 | 1/2018 |
| GB | 2408259 A | 5/2005 |
| GB | 2518646 A | 4/2015 |
| JP | 103139363 A | 6/1991 |
| JP | H04501672 A | 3/1992 |
| JP | 2001502191 A | 2/2001 |
| JP | 2001521792 A | 11/2001 |
| JP | 2004208740 A | 7/2004 |
| JP | 2008532701 A | 8/2008 |
| JP | 2008239164 A | 10/2008 |
| JP | 2010527276 A | 8/2010 |
| JP | 2012522593 A | 9/2012 |
| JP | 2015517377 A | 6/2015 |
| JP | 2016511119 A | 4/2016 |
| JP | 2016104214 A | 6/2016 |
| WO | 0019878 | 4/2000 |
| WO | 200024442 A1 | 5/2000 |
| WO | 200224551 A1 | 3/2002 |
| WO | 2011066586 A1 | 6/2011 |
| WO | 2013046857 A1 | 4/2013 |
| WO | 2014159346 A1 | 10/2014 |
| WO | 2015127285 A1 | 8/2015 |
| WO | 2015174953 A1 | 11/2015 |
| WO | 2016158144 A1 | 10/2016 |
| WO | 2017087400 A1 | 5/2017 |
| WO | 2017095373 A1 | 6/2017 |
| WO | 2018106508 A1 | 6/2018 |
| WO | 2018237090 A1 | 12/2018 |
| WO | 2019147906 A1 | 8/2019 |
| WO | 2019212637 A1 | 11/2019 |
| WO | 2020112767 A1 | 6/2020 |

OTHER PUBLICATIONS

Non-Final Office Action in U.S. Appl. No. 16/774,853 dated Feb. 1, 2022, 12 pages.

PCT International Search Report and Written Opinion in PCT/US2021/027214 dated Jul. 19, 2021, 14 pages.

PCT International Search Report and Written Opinion in PCT/US2021/027218 dated Jul. 22, 2021, 14 pages.

PCT International Search Report and Written Opinion in PCT/US2021/027220 dated Jul. 21, 2021, 15 pages.

PCT Invitation to Pay Additional Fees in PCT/US2021/027219, dated Jul. 22, 2021, 15 pages.

"Non-Final Office Action in U.S. Appl. No. 17/076,102 dated Aug. 24, 2021, 10 pages".

PCT Invitation to Pay Additional Fees in PCT/US2021/019546, dated Jun. 15, 2021, 17 pages.

* cited by examiner

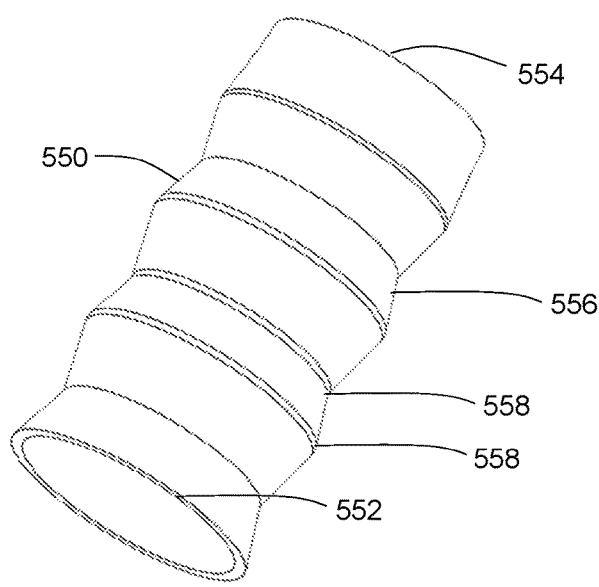
FIG. 11B
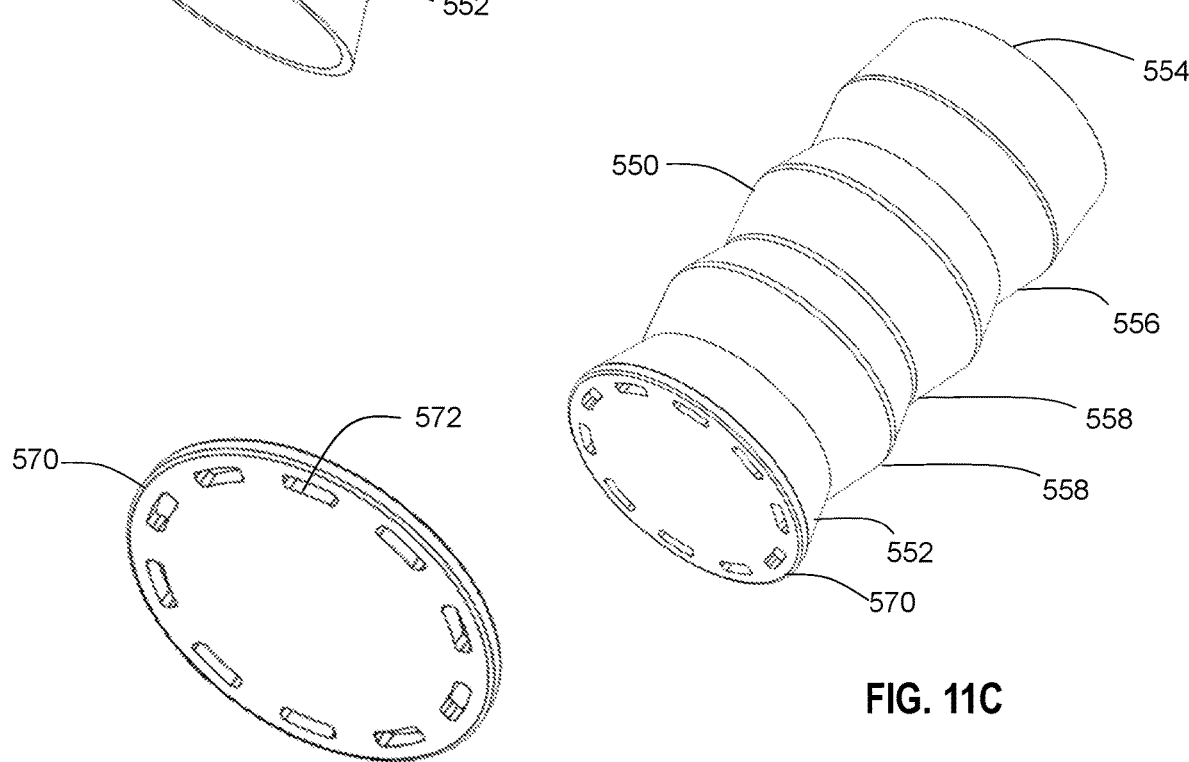
FIG. 11C
FIG. 11D

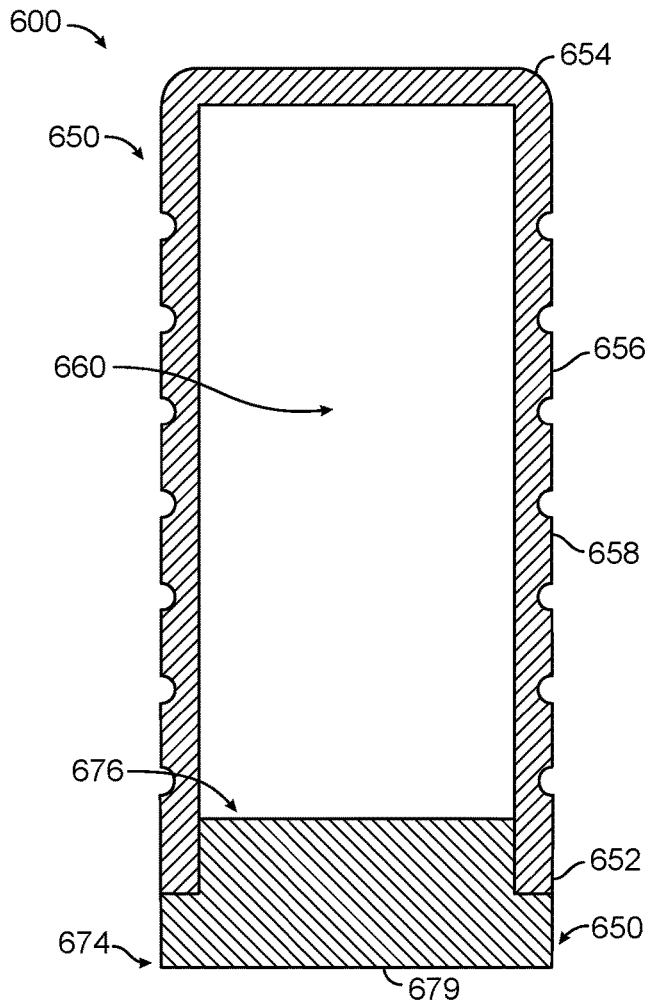
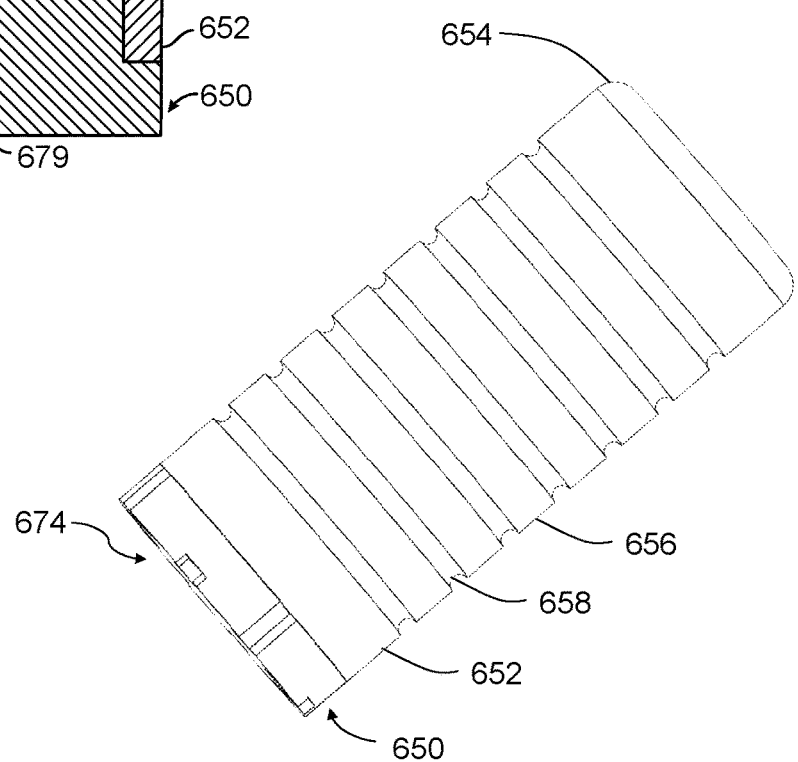
FIG. 15A
FIG. 15B

DISINFECTION CAP

CROSS-REFERENCE TO RELATED APPLICATIONS

This application claims priority to U.S. Provisional Application No. 63/011,357, filed Apr. 17, 2020, the entire disclosure of which is hereby incorporated by reference herein.

TECHNICAL FIELD

The present disclosure relates to disinfection cap devices for disinfecting corresponding medical connectors. The present disclosure generally relates to a device for disinfecting and sterilizing access ports of medical connectors having a fitting. Generally, the present disclosure also relates to the fields of threaded or interlocking fittings, including medical caps and medical disinfection caps, and in particular, caps or disinfection caps for uses with threaded fluid connectors. The present disclosure also relates to male disinfection cap devices for disinfecting male threaded luer connectors.

BACKGROUND

Vascular access devices (VAD's) are commonly used therapeutic devices and include intravenous (IV) catheters. There are two general classifications of VAD's: peripheral catheters and central venous catheters. Bacteria and other microorganisms may gain entry into a patient's vascular system from an access hub, port, or valve upon connection to the VAD to deliver a medical fluid or pharmaceutical. Each access hub, port, valve or connection is associated with some risk of transmitting a catheter related bloodstream infection (CRBSI), which can be costly and potentially lethal. In order to decrease CRBSI cases and to ensure VAD's are used and maintained correctly, standards of practice have been developed, which include disinfecting and cleaning procedures. Disinfection caps have been added to the Society for Healthcare Epidemiology of America (SHEA) guidelines and also the Infusion Nurses Standards (INS) guidelines.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface that possibly lead to a variety of catheter related complications including CRBSI. Nurses will typically utilize a 70% isopropyl alcohol (IPA) pad to complete this disinfection task by doing what is known as "scrubbing the hub." However, compliance to this practice is typically very low. In addition to a lack of compliance to "scrubbing the hub", it has also been noted through clinician interviews that there is often a variation in scrub time, dry time and the number of times the needleless connector is scrubbed.

The need to protect female and male luer connectors to reduce central line-associated bloodstream infections (CLABSI) and peripheral line-associated bloodstream infection (PLABSI) has been rising. Intravenous gravity sets and threaded male luer connections on syringes are subject to contamination when not protected properly. Currently when IV connectors are disconnected from central lines or peripheral lines to temporarily discontinue infusion, nurses often loop the male luer connector to a Y-site needle-free connector or wrap the male luer connector in a piece of Isopropyl Alcohol ("IPA") impregnated wipe or cloth. However, such protection is very weak and does not properly protect the luer from touch contamination. Male disinfection caps have become the state of art disinfection and protection device to disinfect and create a physical barrier on male luer connector to prevent microbial growth.

Throughout the sequence of procedures associated with the transmission of a microorganism that can cause a CRBSI, there are many risks of contact or contamination. By way of example, contamination can occur during drug mixing, attachment of a cannula, and insertion into the access hub. Furthermore, threaded male luer connectors have an open luer with an exposed lumen. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable.

Disinfectants typically have a threshold limit for systemic exposure for infusion into blood stream due to biotoxicity of the disinfectants at high dosage. Thus, there is a need for a disinfection device capable of blocking the lumen of open luers to facilitate the mitigation of such disinfectant ingress into connectors, thereby reducing risk of the disinfectant entering the blood stream. There is a need for a mechanism to prevent disinfectant from entering the lumen and fluid path while providing effective disinfection of the surrounding connector or fitting.

SUMMARY

A first aspect of the present disclosure relates to a disinfection cap having a cylindrical sidewall, a cavity and an open bottom. The cylindrical sidewall has an inner surface which defines the cavity and a top wall. The open bottom is formed by the cylindrical sidewall with an opening to the cavity within said housing for receiving a hub of a luer connector. The disinfection cap further comprises a retention rod disposed within the cavity, the retention rod having a proximal flange, a distal flange and an elongated rod between the proximal flange and distal flange, the distal flange of the retention rod abutting the top wall of the cavity. A fluid reservoir is defined between the inner surface of the housing, the proximal flange of the retention rod and the distal flange of the retention rod. A disinfectant is disposed within the fluid reservoir, the disinfectant being retained within the fluid reservoir in an initial state. The hub of said luer connector is received within said inner surface of said cavity.

In one or more embodiments, a diameter of the proximal flange of the retention rod is equal to or slightly larger than a diameter of a proximal portion of the cavity, configured to have an interference fit sufficient to create a fluid seal between the proximal flange of the retention rod and the proximal portion of the cavity.

In one or more embodiments, a diameter of the elongated rod is configured to buckle to a final state upon insertion of a hub of the luer connector when the hub of the luer connector is received within the cavity, thereby breaking the fluid seal between the proximal flange and the proximal portion of the cavity and releasing disinfectant into the cavity disinfecting the hub and a periphery of the luer connector.

In one or more embodiments, at least one circular fin is disposed on the elongated rod, the at least one fin having a thickness configured to elastically deform, whereby pressure buildup within the fluid reservoir due to insertion of the luer connector causes deformation of the at least one fin.

In one or more embodiments, a diameter of the elongated rod is configured to compress upon insertion of the hub of the luer connector when the hub of the luer connector is received within the cavity.

In one or more embodiments, a diameter of the distal flange is equal to or larger than a diameter of a distal portion of the cavity, configured to create an interference fit sufficient enough to removably hold the retention rod within the cavity.

In one or more embodiments, the distal flange of the retention rod is bonded to the top wall of the cavity. In one or more embodiments, the distal flange of the retention rod is chemically bonded to the top wall of the cavity. In one or more embodiments, the distal flange of the retention rod is unitarily formed with the top wall of the cavity.

In one or more embodiments, the hub of the luer connector is received within the inner surface of the cavity. In one or more embodiments, the disinfection cap is secured by at least one thread or set of tabs included on an outer surface of the housing, the at least one thread being sized and have a thread pattern that will engage with a standard ISO-2 type of luer fitting. In one or more embodiments, when the hub of the luer connector is received within the inner surface of the cavity, the hub is secured within the cavity of the disinfection cap by interlocking at least a portion of the at least one thread with a mating feature on the hub of the luer connector. In one or more embodiments, the cavity is configured to facilitate a loose fit between the cavity and the hub of the luer connector.

A second aspect of the present disclosure relates to a disinfection cap having a cylindrical sidewall, a cavity, an open bottom and a corrugated capsule disposed within the cavity. The cylindrical sidewall has an inner surface defining the cavity and a top wall. An open bottom formed is by the cylindrical sidewall with an opening to the cavity within said housing for receiving a hub of a luer connector. The corrugated capsule has a proximal surface, a distal surface and an elongated body between the proximal surface and distal surface, the distal surface of the corrugated capsule abutting the top wall of the cavity, the corrugated capsule having a fluid reservoir. A disinfectant is disposed within the fluid reservoir, the disinfectant being retained within the fluid reservoir in an initial state. The hub of said luer connector is received within said inner surface of said cavity.

In one or more embodiments, the elongated body further comprising at least one or more corrugations configured to collapse on one another upon application of pressure on the proximal surface due to insertion of the hub into the cavity of the housing.

In one or more embodiments, the corrugated capsule further comprises a slit in fluid communication with a fluid reservoir, the slit being disposed on the proximal surface of the corrugated capsule. In one or more embodiments, wherein in an initial, uncompressed state, the slit is fluidly closed, the fluid reservoir retaining disinfectant due to negative pressure within the fluid reservoir. In one or more embodiments, upon compression of the elongated body due to insertion of the hub of the luer connector, the at least one corrugation collapses on one another causing a pressure buildup within the reservoir, the pressure buildup causing the slit to deform and open, causing disinfectant to eject from the slit, disinfecting the hub and a periphery of the luer connector.

In one or more embodiments, the corrugated capsule further comprises a plurality of perforations in fluid communication with a fluid reservoir, the plurality of perforations being disposed on the elongated body of the corrugated capsule. In one or more embodiments, the plurality of perforations are arranged in at least one row of perforations, the at least one row of perforations being disposed longitudinally on the elongated body.

In one or more embodiments, in an initial, uncompressed state, the plurality of perforations are fluidly closed and the fluid reservoir retains disinfectant due to negative pressure within the fluid reservoir.

In one or more embodiments, upon compression of the elongated body due to insertion of the hub of the luer connector, the at least one corrugation collapses on one another causing a pressure buildup within the reservoir, the pressure buildup causing the plurality of perforations to deform and open, causing disinfectant to eject from the plurality of perforations, disinfecting the hub and a periphery of the luer connector.

In one or more embodiments, the distal surface of the corrugated capsule further comprises an aperture extending through the distal surface.

In one or more embodiments, the proximal surface of the corrugated capsule is an open proximal surface. In one or more embodiments, the disinfection cap further comprises an end cap abutting an engagement surface of the open proximal surface. In one or more embodiments, the end cap comprises a plurality of apertures, the plurality of apertures are configured to be disposed around a periphery of the end cap. In one or more embodiments, the plurality of apertures are positioned a distance away from a center of the end cap as to not direct fluid flow into a lumen of the hub of the luer connector.

In one or more embodiments, wherein in an initial, uncompressed state, the plurality of apertures are configured to not excrete disinfectant due to negative pressure within the fluid reservoir. In one or more embodiments, wherein in a final, compressed state, the buildup of pressure causes disinfectant to excrete through the plurality of apertures, disinfecting the hub and the periphery of the luer connector.

A third aspect of the present disclosure relates to a disinfection cap having a cylindrical sidewall, a cavity and a corrugated capsule disposed within the cavity. The cylindrical sidewall has an inner surface defining the cavity and a top wall. An open bottom is formed by the cylindrical sidewall with an opening to the cavity within said housing for receiving a hub of a luer connector. The corrugated capsule is disposed within the cavity, the corrugated capsule having an open proximal end, a closed distal end and an elongated body between the open proximal end and closed distal end, the distal end of the corrugated capsule abutting the top wall of the cavity, the corrugated capsule having a fluid reservoir. A disinfectant is disposed within the fluid reservoir, the disinfectant being retained within the fluid reservoir in an initial state. A piston disposed against the open proximal end. The hub of said luer connector is received within said inner surface of said cavity.

In one or more embodiments, the elongated body further comprises at least one corrugation configured to collapse on one another upon application of pressure on the proximal surface due to insertion of the hub into the cavity of the housing.

In one or more embodiments, the housing further comprises dual winged protrusions disposed on a distal portion of the housing.

In one or more embodiments, the piston comprises a proximal portion and a distal portion, the proximal portion having a diameter equal to or slightly less than a diameter of the corrugated cap, a diameter of the distal portion substantially equal to a diameter of the fluid reservoir, the diameter of the distal portion being configured to be positioned within the corrugated capsule, creating a liquid tight seal.

In one or more embodiments, the piston further comprises a plurality of apertures extend from the distal portion of the corrugated capsule to the proximal end of the corrugated capsule, the plurality of apertures being in fluid communication with the fluid reservoir and are configured to eject disinfectant upon compression of the corrugated capsule.

In one or more embodiments, the piston further comprises a plurality of directional channels disposed on a proximal surface of the proximal portion of the piston, the plurality of directional channels being configured to direct disinfectant towards a periphery of the luer hub of the luer connector.

In one or more embodiments, the plurality of directional channels are configured to be disposed around a periphery of the proximal surface of the piston, the plurality of directional channels being positioned a distance away from a center of the proximal surface as to not direct fluid flow into a lumen of the hub of the luer connector.

BRIEF DESCRIPTION OF THE DRAWINGS

FIGS. 11A through 11C illustrate perspective views of the corrugated capsule of the disinfection cap of FIG. 10;

FIG. 11D illustrates a perspective view of the end cap of the disinfection cap of FIG. 10;

FIG. 15A illustrates a cross-sectional view of a corrugated capsule and the piston of the disinfection cap of FIG. 13A; and FIG. 15B illustrates a perspective view of the corrugated capsule and the piston of the disinfection cap of FIG. 13A.

DETAILED DESCRIPTION

Figure 1:
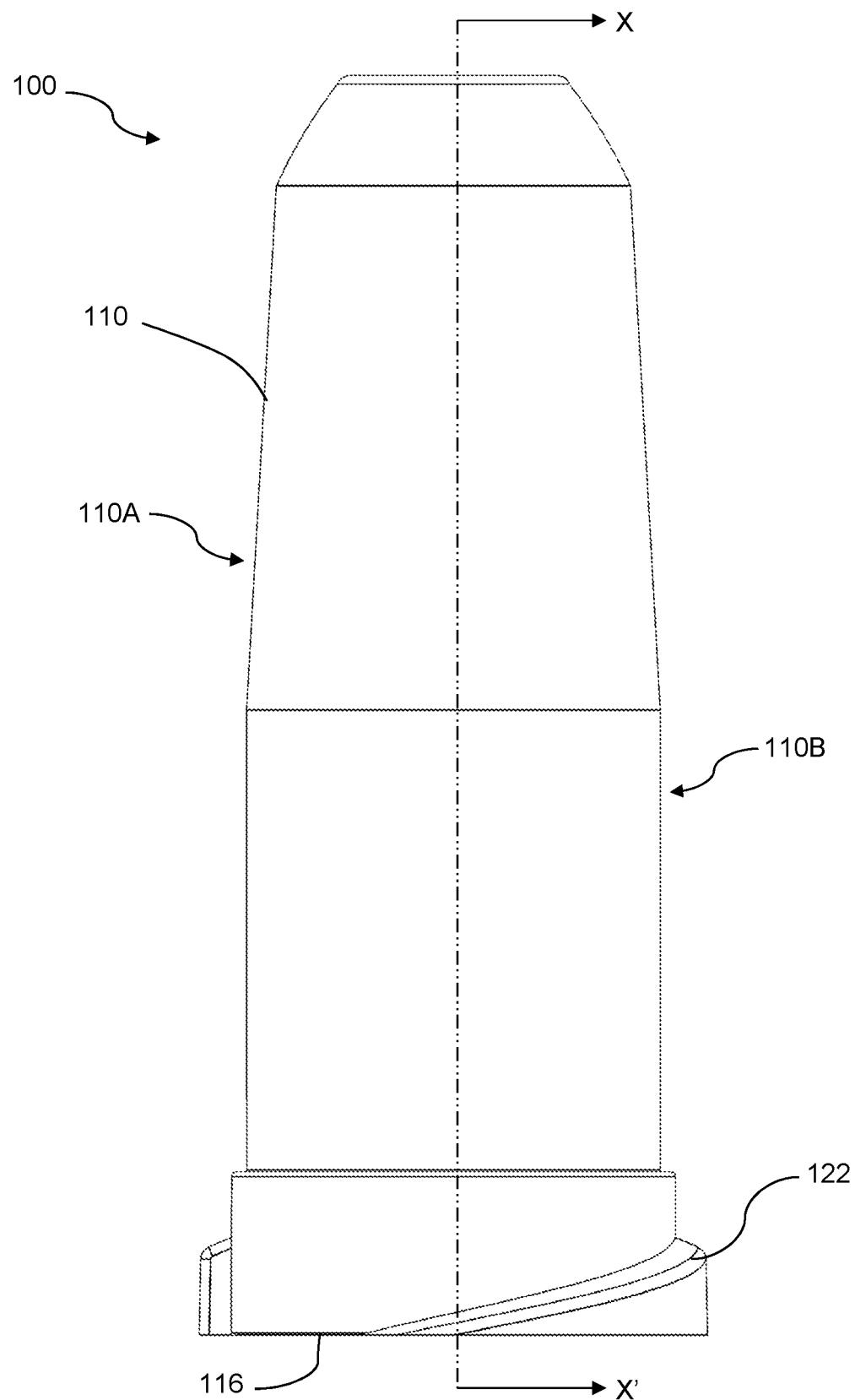
FIG. 1 illustrates a front view of a disinfection cap according to an exemplary first embodiment of the present disclosure.

Embodiments of the disclosure pertain to a disinfection cap for connection to and disinfection of a medical connector, including threaded connections. In one or more embodiments, the medical connector is a luer connector or a needleless connector. In one or more embodiments, the medical connector is a male luer connector. In one or more embodiments, the medical connector is a female luer connector. The disclosure aims to provide a mechanism to prevent disinfectant from entering the fluid path of the medical connector while providing for effective disinfection for the hub and surrounding periphery of the medical connector.

Before describing several exemplary embodiments of the disclosure, it is to be understood that the disclosure is not limited to the details of construction or process steps set forth in the following description. The disclosure is capable of other embodiments and of being practiced or being carried out in various ways.

For purposes of the description hereinafter, the terms "top", "bottom", "longitudinal", and derivatives thereof shall relate to the disclosure as it is oriented in the drawing figures. However, it is to be understood that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the embodiments disclosed herein are not to be considered as limiting.

As used herein, the use of "a," "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of one or more interlocking tubes, slightly tapered to hold together with just a simple pressure/twist fit. Luer connectors can optionally include an additional outer rim of threading, allowing them to be more secure. The Luer connector is generally associated with a flush syringe and can interlock and connect to the end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe. As used herein, the term "Luer connector" refers to a male luer connector or a female luer connector.

As used herein, the term "medical device" refers to common medical devices having threaded or interlocking connections, the connections having corresponding mating elements. By way of example but not limitation, a syringe may have a threaded connection which releasably interlocks with a secondary medical device such as a needleless connector of a catheter, an IV line and the like. The threaded connection may include a lumen defining a fluid path surrounded by a protruding wall having the threaded means for attaching to the secondary medical device.

As would be readily appreciated by skilled artisans in the relevant art, while descriptive terms such as "thread", "taper", "tab", "wall", "top", "side", "bottom" and others are used throughout this specification to facilitate understanding, it is not intended to limit any components that can be used in combinations or individually to implement various aspects of the embodiments of the present disclosure.

Embodiments of the disinfection cap of the present disclosure comprise a housing having a top wall defining a closed distal end, an open proximal end, and a substantially cylindrical sidewall extending from the closed end to the open proximal end, the sidewall having an inner surface. The cavity is configured for receiving a hub of a needleless connector. In one or more embodiments, the cavity is configured for receiving a hub of a threaded needleless connector. In one or more embodiments, the disinfection cap having at least one thread on an exterior surface of the cylindrical sidewall that is sufficient to interlock with a mating feature of the threaded connection. Embodiments of the disinfection cap disclose the at least one thread of the disinfection cap engaging the mating feature of the threaded connection, and more specifically a luer connection. The cap further comprises a capsule having perforations functioning as a disinfectant reservoir configured to release a disinfectant fluid upon insertion of the hub of the needleless connector. The capsule is further configured as a blockage feature to fluidly block an open lumen of a luer to prevent ingress of disinfectant into the open luer upon insertion of the luer connector into the cavity of the housing. In one or more embodiments, open proximal end of the housing includes a peripheral ledge extending radially outward from the outer surface of the sidewall defining an end face and an engagement surface for a removable seal and/or septum for maintaining sterility of the cavity. The removable seal reduces or prevents contamination of the cavity during shipping and storage of the disinfection cap. The removable seal is generally kept sealed in the pre-activated state until just prior to connection to a VAD, or an injection and/or aspiration procedure, at which time the peelable seal is removed. The removable seal minimizes entry of potential particulate hazard and also provides a substantially impermeable enclosure for the cavity prior to use of the disinfection cap. The removable seal provides a sufficient seal at a range of temperatures, pressures, and humidity levels. In one or more embodiments, the removable seal is a peel seal.

The disinfection cap provides a mechanical barrier for connectors and contains a disinfectant fluid or an antimicrobial agent (hereinafter "fluid"). The disinfection cap of the present disclosure allows the practitioner to streamline the disinfecting process. The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

In particular, the practitioner may disinfect the needleless connector in a single motion by inserting or threading the disinfection cap onto the needleless connector of the medical device which causes the blockage feature to prevent fluid ingress into the fluid path of the hub of the needleless connector, while the insertion of the hub of the luer connector simultaneously causes the release of the fluid allowing for disinfection of the luer connector hub and its periphery. In one or more embodiments, the disinfection cap may then be removed by removing or unthreading the disinfection cap from the luer connector. In one or more embodiments, the disinfection cap may remain connected to the luer connector until ready for use, providing for a disinfected, closed environment.

In an exemplary implementation of the embodiments of present disclosure, the disinfection cap includes integrated threads or tabs, and other features in any and all combinations allowing it to interface with a threaded fitting of a medical device. In preferred embodiments, the disinfection cap interfaces with a Luer fitting. Exemplary configurations for couplers, fittings, ports and adapters may include commercially available luer locks, luer slip ports, locking ports, threaded connections, interlocking connection or generally other common medical device fitting known in the art.

Referring now to the drawings, wherein like reference numerals designate identical or corresponding parts throughout the several views, embodiments of the present disclosure are described as follows.

Figure 2:
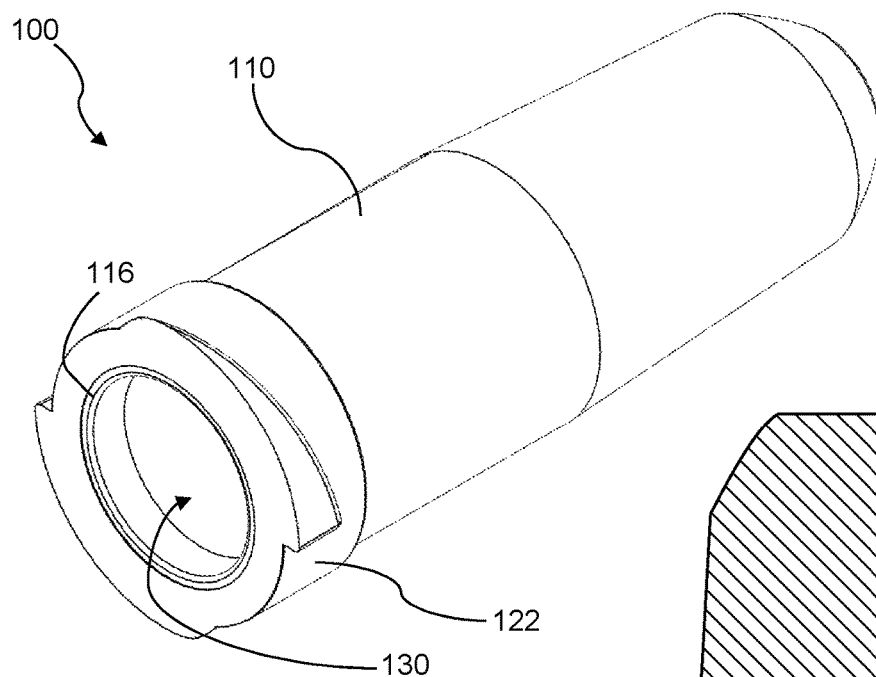
FIG. 2 illustrates a side perspective view front view of the disinfection cap of FIG. 1 in accordance with the first embodiment.

As depicted in FIGS. 1, 2A and 2B, a first embodiment of the present disclosure relates to a disinfection cap 100 including a housing 110, the housing 110 having a distal portion 110A and a proximal portion 110B. In one or more embodiments, the proximal portion 110B is substantially cylindrical. In one or more embodiments, the proximal portion 110B is be tapered. In one or more embodiments, the distal portion 110A of the housing is tapered. In further embodiments, the distal portion 110A and proximal portion 110B are substantially cylindrical. In one or more embodiments, an inner surface 126 of the proximal portion 110B of the housing 110 defines a cavity 130 having open bottom 116 for receiving a hub of a needleless connector or more specifically a luer connector. In one embodiment, distal portion 110A is integrally formed with the proximal portion 110B. While further alternate embodiments are non-removably or removably assembled with a threaded connection, press-fit connection, adhesive connection or a combination thereof.

Figure 3A:
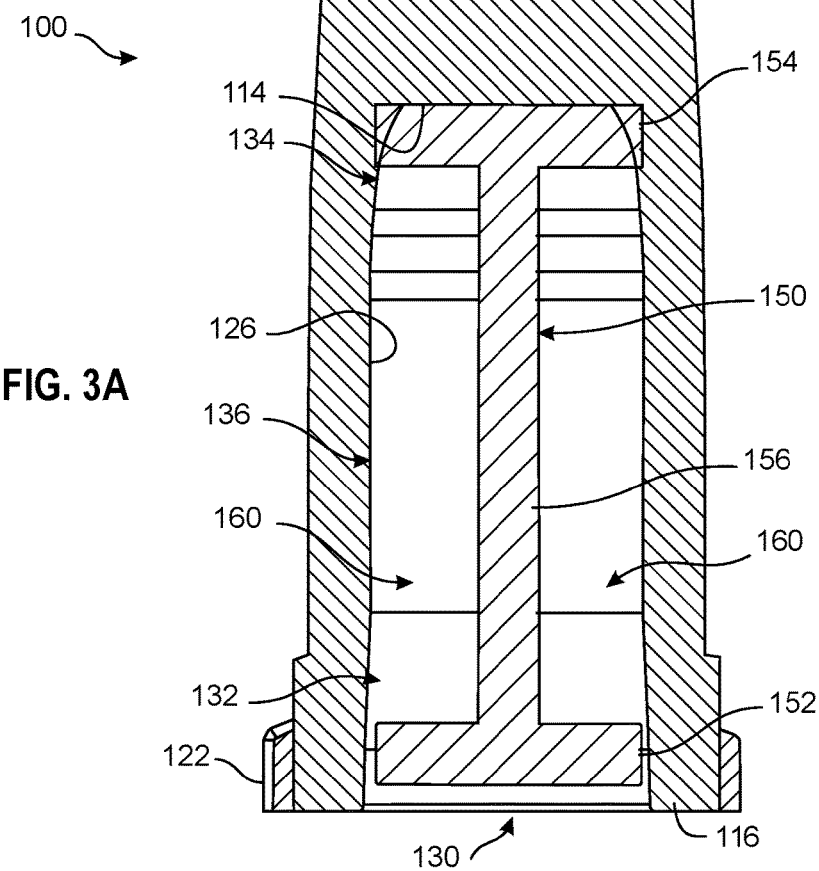
FIG. 3A illustrates a cross sectional view of a retention rod disposed within the disinfection cap along the axis X-X' of the disinfection cap of FIG. 1.

As shown in FIG. 3A, the cavity 130 has a proximal portion 132, a distal portion 134, and a medial portion 136 between the proximal portion 132 and the distal portion 134. In one or more embodiments, the proximal portion 132 has an inwardly tapered shape, tapering inward from the open bottom 116 to the medial portion 136. In one or more embodiments, the distal portion 134 has a cylindrical shape. The medial portion 136 has a cylindrical shape. The distal portion 134 has a rounded or inwardly tapered shape, tapering inward from the medial portion 136 to the top wall 114. In one or more embodiments, the distal portion 134 has a rounded or chamfered transition from the distal portion 134 to the top wall 114.

In one or more embodiments, the cavity 130 is be configured to facilitate a loose fit between the cavity 130 and the hub of the luer connector, wherein the disinfection cap 100 is secured by an at least one thread 122 or set of tabs included on an outer surface of the housing 110, the at least one thread 122 being disposed on the proximal portion 110B. The at least one thread 122 disposed on the outer surface of the housing 110 is sized and have a thread pattern that will engage with a standard ISO-2 type of luer fitting. The loose fit allows for fluid to flow around the hub of the luer connector. In further embodiments, the cavity 130 is configured as a Luer Slip fitting to facilitate an interference fit between the cavity 130 and the hub of the luer connector. In one or more embodiments, the interference fit is configured to be sufficiently strong enough to not require a threaded connection or the at least one thread 122 in removably securing the cavity 130 to the luer connector.

In one or more embodiments, when the hub of the luer connector is received within the inner surface 126 of the cavity 130, the hub is secured within the cavity 130 of the disinfection cap 100 by interlocking at least a portion of the at least one thread 122 with a mating feature on the hub of the luer connector. In one or more embodiments, the at least one thread 122 can include an inclined thread pattern. In one or more embodiments, the at least one thread 122 can include a helical-shaped thread pattern. Such connectors are generally and commonly used as catheter and other fluid-tight protective connectors in medical applications. In some embodiments, the disinfection cap 100 provides a protective cover for a luer connector when engaged with the connector when threads from the luer connector engage and form a releasable connection with at least one thread 122 of disinfection cap 100.

Figure 3B:
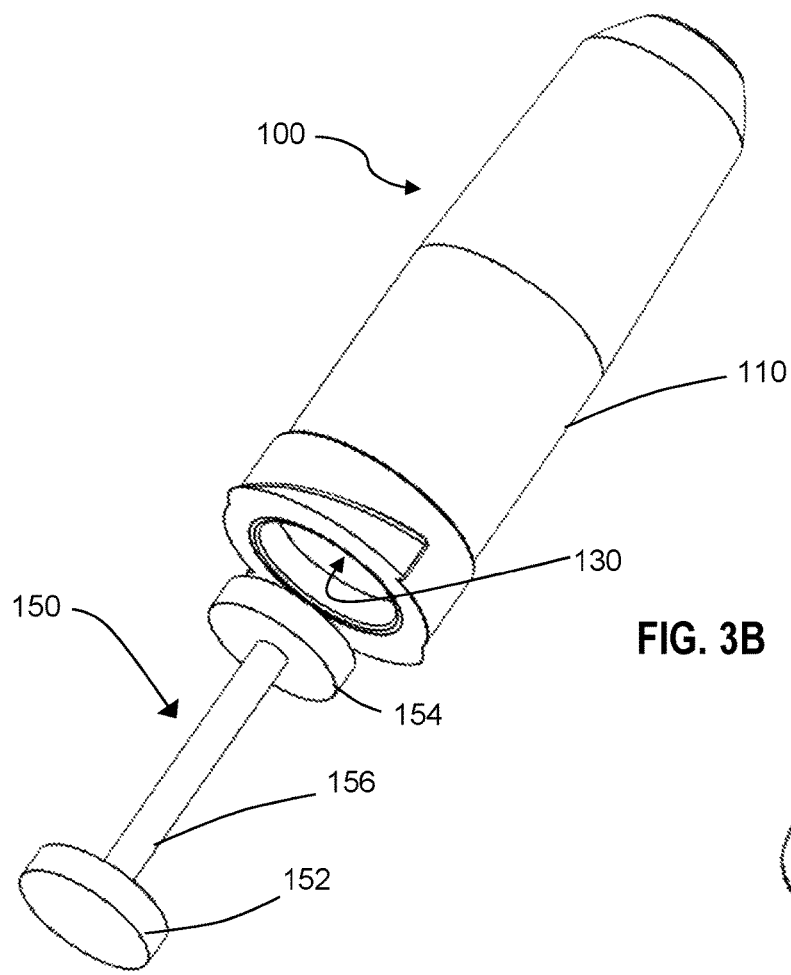
FIG. 3B illustrates a perspective exploded view of the disinfection cap of FIG. 1 in accordance with the first embodiment.

FIG. 3A depicts a cross-sectional view of the disinfection cap 100 along an X-X' plane as shown in FIG. 1. FIG. 3B depicts an exploded view of the disinfection cap 100, the disinfection cap having a retention rod 150 disposed within. As depicted in FIGS. 3A and 3B, cavity 130 of the housing 110 extends a length of the total length of the housing 110 from the open bottom 116 to a top wall 114. The cavity 130 has a substantially cylindrical shape. Disposed within the cavity 130 is the retention rod 150 configured as a fluid reservoir 160 for retaining disinfectant. The retention rod comprises a proximal flange 152, a distal flange 154 and an elongated rod 156 extending from the proximal flange 152 and the distal flange 154. The retention rod 150 has a height from the proximal flange 152 to the distal flange 154, the height being equal to or slightly less than a height of the cavity 130. In one or more embodiments, the proximal flange 152 and the distal flange 154 have an equal diameter.

In one or more embodiments, the diameter of the proximal flange 152 is smaller than the diameter of the distal flange 154.

As shown in FIGS. 3B and 3C, the retention rod 150 is disposed within the cavity 130 of the housing 110. The distal flange 154 abuts the top wall 114. The fluid reservoir 160 is defined between the inner surface 126 of the housing 110, the proximal flange 152 and the distal flange 154. The diameter of the proximal flange 152 is equal to or slightly larger than a diameter of the proximal portion 132 of the cavity 130, creating an interference fit sufficient to create a fluid seal between the proximal flange 152 and the proximal portion 132 of the cavity 130. The diameter of the distal flange 154 is equal to or larger than a diameter of the distal portion 134, creating an interference fit sufficient enough to removably hold the retention rod 150 within the cavity 130. In one or more embodiments, the retention rod 150 is unitarily formed to the housing 110, connecting the distal flange 154 to the top wall 114 of the housing 110. In one or more embodiments, the distal flange 154 is chemically bonded with adhesive to the top wall 114 of the housing 110.

Figure 4A:
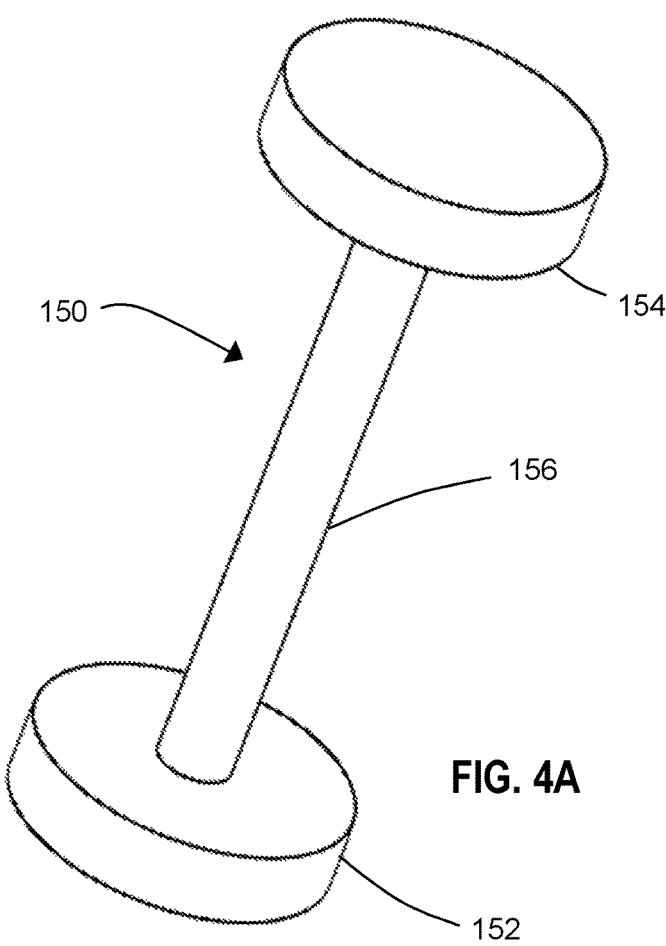
FIG. 4A illustrates a perspective view of a retention rod disposed within the disinfection cap of FIG. 1, in accordance with the first embodiment.
Figure 4B:
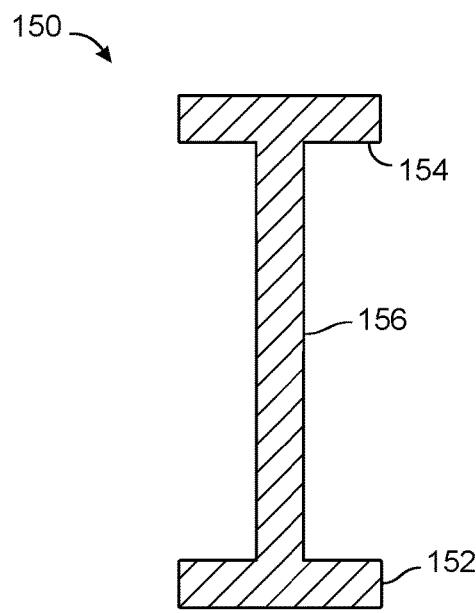
FIG. 4B through 4D illustrate side views of the retention rod of the disinfection cap of FIG. 1.
Figure 4C:
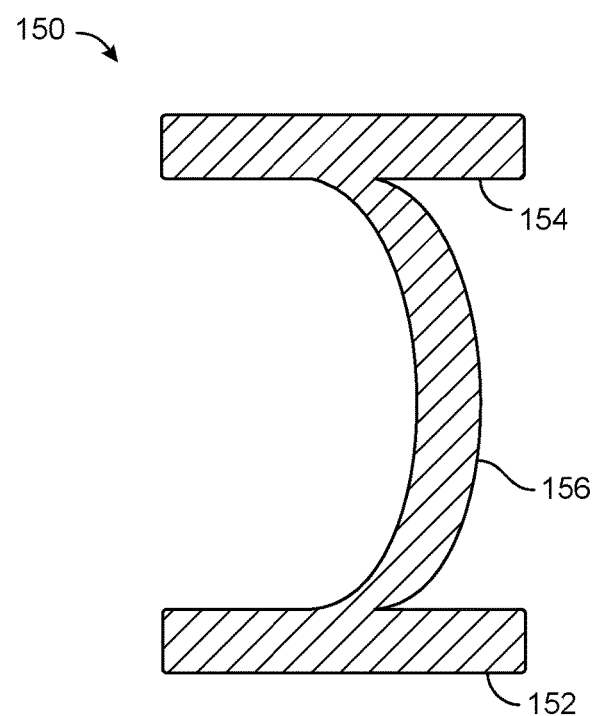

As shown in FIGS. 4A through 4C, the elongated rod 156 is configured to buckle upon insertion of a hub of a luer connector when the hub of the luer connector is received within the cavity 130. In an initial, unbuckled state as shown in FIGS. 3A and 4B, the retention rod 150 retains disinfectant within the fluid reservoir 160. In a final, buckled state shown in FIG. 4C, the elongated rod 156 buckles and elastically deforms, thereby breaking the fluid seal between the proximal flange 152 and the proximal portion 132 of the cavity 130. Breaking of the fluid seal opens the fluid reservoir, releasing disinfectant into the cavity 130 and disinfecting the hub and the periphery of the luer connector. In one or more embodiments, as shown in FIG. 4C, the proximal flange 152 deflects, thereby breaking the fluid seal between the proximal flange 152 and the proximal portion 132 of the cavity 130.

In one or more embodiments, the proximal flange 152 conforms to the hub of the male luer connector upon insertion of the male luer connector. In one or more embodiments, the elongated rod 156 buckles into a toroid structure, while the proximal flange 152 does not rotate.

Figure 4D:
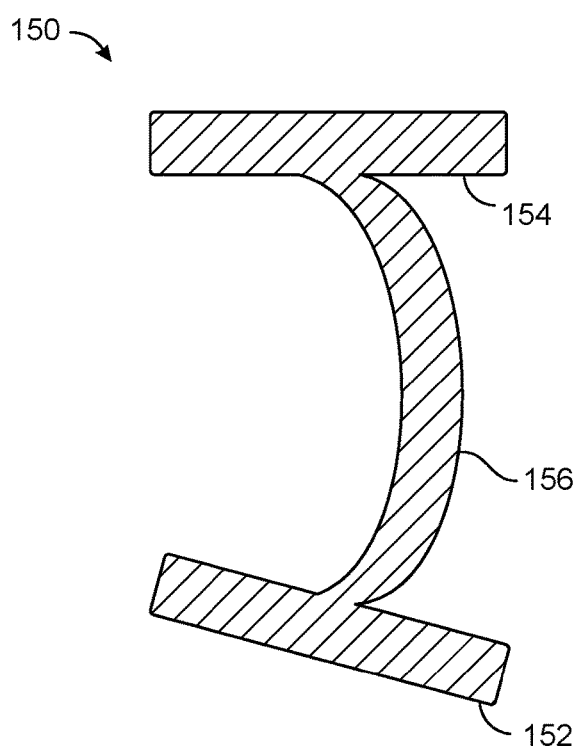

In an alternative embodiment, compression of the retention rod 150 causes the proximal flange 152 to buckle and rotate, as depicted in FIG. 4D.

In some embodiments, the retention rod 150 is of a flexible TPE material or more generally a non-rigid plastic allowing the retention rod 150 to flex and buckle upon pressure application due to insertion of the luer connector into the cavity 130.

In accordance with a second embodiment of the present disclosure, and as shown in FIGS. 5 and 6A through 6C, an exemplary retention rod 250 of a disinfection cap 200 of a second embodiment is disclosed. The retention rod 250 of the second embodiment is disposed within the cavity 130 of the housing 110. The retention rod 250 comprises a proximal flange 252, a distal flange 254, an elongated rod 256 extending from the proximal flange 152 and the distal flange 154, and at least one circular fin 258 disposed on the elongated rod 256. The distal flange 254 abuts the top wall 114 of the housing 110. The retention rod 250 has a height from the proximal flange 252 to the distal flange 254, the height being equal to or slightly less than a height of the cavity 130. In one or more embodiments, the proximal flange 252 and the distal flange 254 have an equal diameter. In one or more embodiments, the diameter of the proximal flange 252 is smaller than the diameter of the distal flange 254. The at least one circular fin 258 has a diameter less than or equal to a diameter of the medial portion 136 of the cavity 130.

In one or more embodiments, the diameter of the at least one circular fin 258 is configured to create an interference fit with the medial portion 136 of the cavity 130. In one or more embodiments, the interference fit of the at least one circular fin 258 and the medial portion 136 create a fluid tight seal. In one or more embodiments, the at least one circular fin 258 is configured to deflect and elastically deform, thereby breaking the fluid tight seal between the at least one circular fin 258 and the medial portion 136. In one or more embodiments, the at least one circular fin 258 support the structure of the retention rod 250 and provide rigidity. In one or more embodiments, the at least one circular fin 258 are configured to be flexible enough to allow for fluid to leak upon compression, but not fully blocking the fluid upon pressure buildup. The at least one circular fin 258 is configured to increase surface area and to increase surface tension to better retain the fluid.

Figure 5:
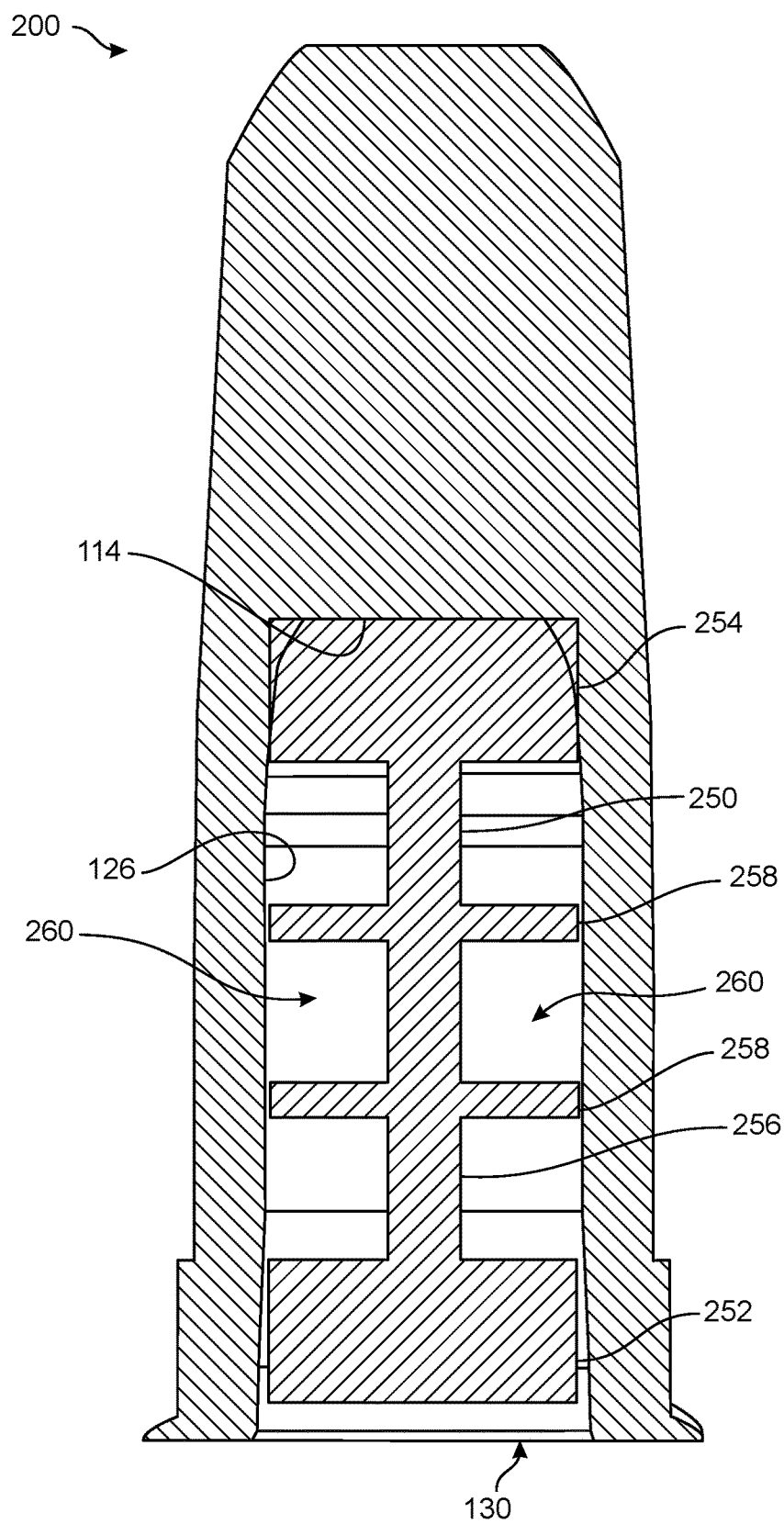
FIG. 5 illustrates a cross-sectional front view of a disinfection cap and a retention rod disposed within the disinfection cap, according to an exemplary second embodiment of the present disclosure.
Figure 6A:
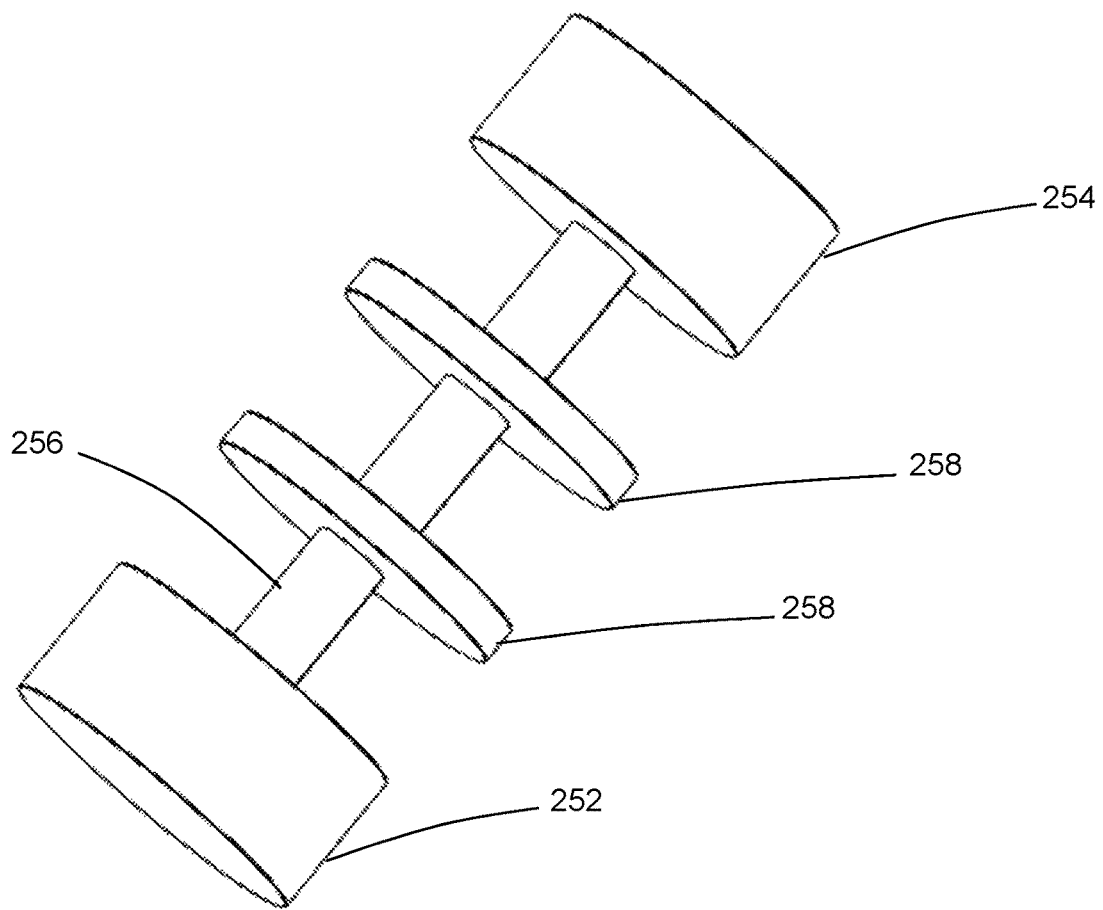
FIG. 6A illustrates a perspective view of the retention rod, in accordance with the second embodiment of the present disclosure.
Figure 6B:
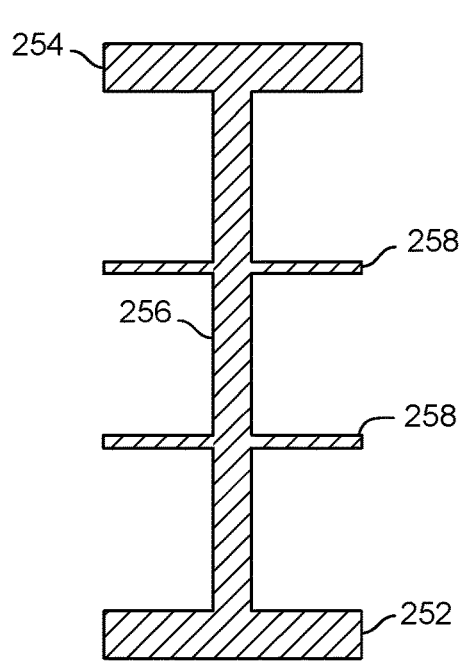
FIG. 6B illustrate side views of the retention rod of the disinfection cap of FIG. 5 in an initial, un-compressed state.
Figure 6C:
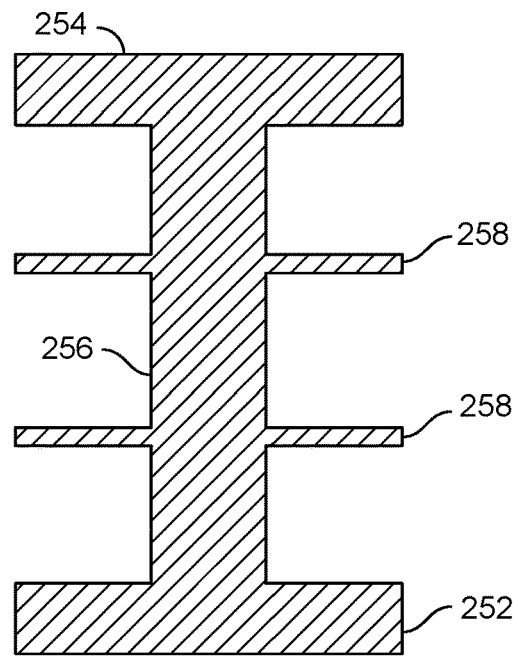
FIG. 6C illustrate side views of the retention rod of the disinfection cap of FIG. 5 in a final, compressed state.
Figure 7:
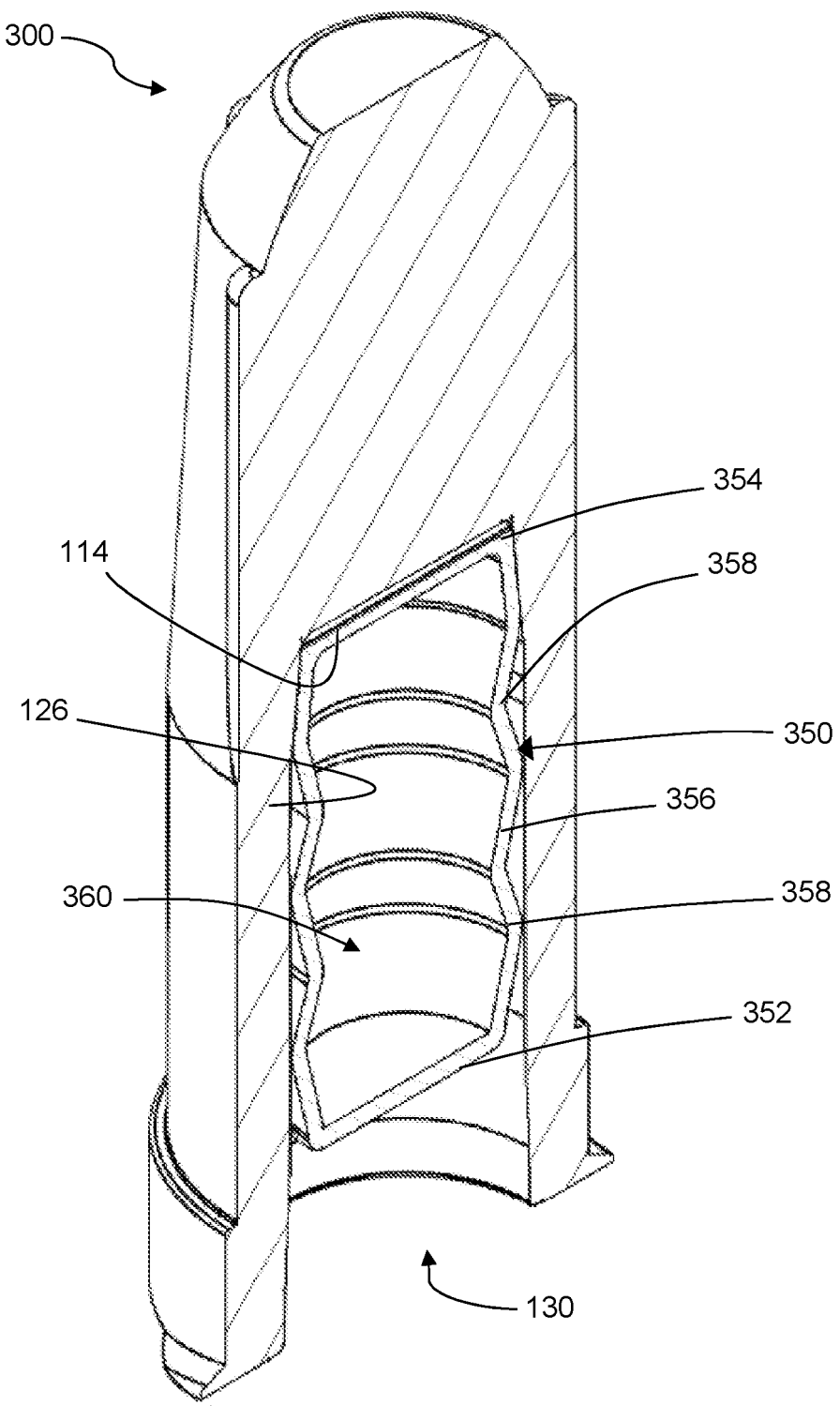
FIG. 7 illustrates a side perspective cross-sectional view of a disinfectant cap and a corrugated capsule disposed within, according to an exemplary third embodiment of the present disclosure.

As shown in FIGS. 6A through 6C, a diameter of the elongated rod 256 is configured to compress upon insertion of the hub of the luer connector when the hub of the luer connector is received within the cavity 130. In an initial, uncompressed state as shown in FIGS. 5, 6A and 6B, the retention rod 250 retains disinfectant within the fluid reservoir 260. In a compressed state shown in FIG. 6C, the elongated rod 256 compresses and elastically deforms, thereby breaking the fluid seal between the proximal flange 252 and the proximal portion 232 of the cavity 130. Breaking of the fluid seal opens the fluid reservoir, releasing disinfectant into the cavity 230 and disinfecting the hub and the periphery of the luer connector. In one or more embodiments, as shown in FIG. 6C, the proximal flange 252 deflects, thereby breaking the fluid seal between the proximal flange 252 and the proximal portion 232 of the cavity 130. The at least one fin 258 has a thickness configured to elastically deform, whereby pressure build up within the fluid reservoir 260 causes deformation of the at least one fin 258. The retention rod 150 is of a flexible TPE material configured to flex and buckle.

In accordance with a third embodiment of the present disclosure, and as shown in FIGS. 7 and 8A through 8C, an exemplary corrugated capsule 350 of a disinfection cap 300 of a third embodiment is disclosed. The corrugated capsule 350 of the third embodiment is disposed within the cavity 130 of the housing 110. The corrugated capsule 350 comprises a proximal surface 352, a distal surface 354, an elongated cylindrical body 356 extending from the proximal surface 352 and the distal surface 354. The distal surface 354 abuts the top wall 114 of the housing 110. The elongated body 356 includes at least one corrugation 358 configured to collapse on one another upon application of pressure on the proximal surface 352 due to insertion of a luer connector hub into the cavity 130 of the housing 120. The elongated body 356 has a height from the proximal surface 352 to the distal surface 354, the height being equal to or slightly less than a height of the cavity 130. In one or more embodiments, the proximal surface 352 and the distal surface 354 have an equal diameter. In one or more embodiments, the diameter of the proximal surface 352 is smaller than the diameter of the distal surface 354.

Figure 8A:
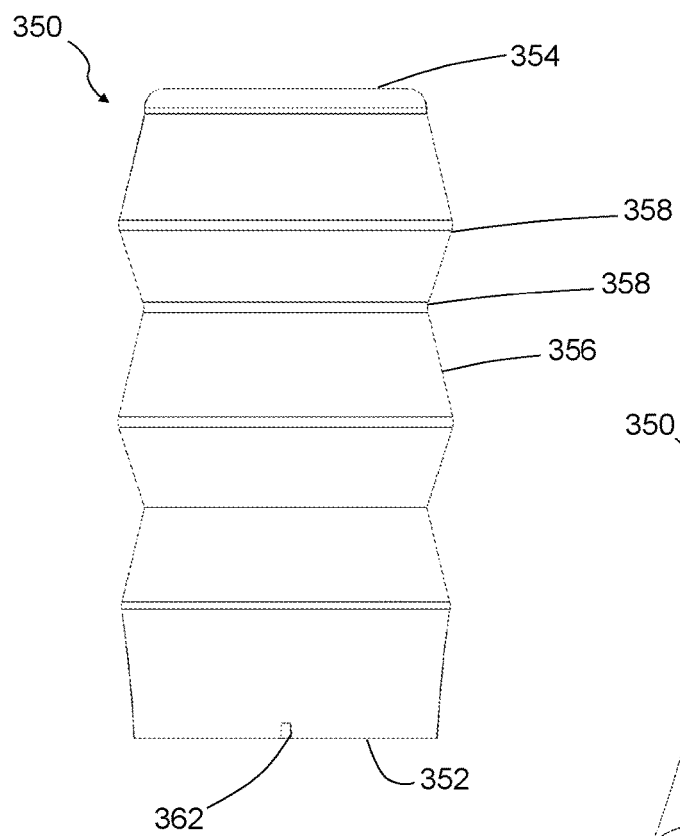
FIG. 8A through 8C illustrate perspective views of the corrugated capsule of the disinfection cap of FIG. 7.
Figure 8B:
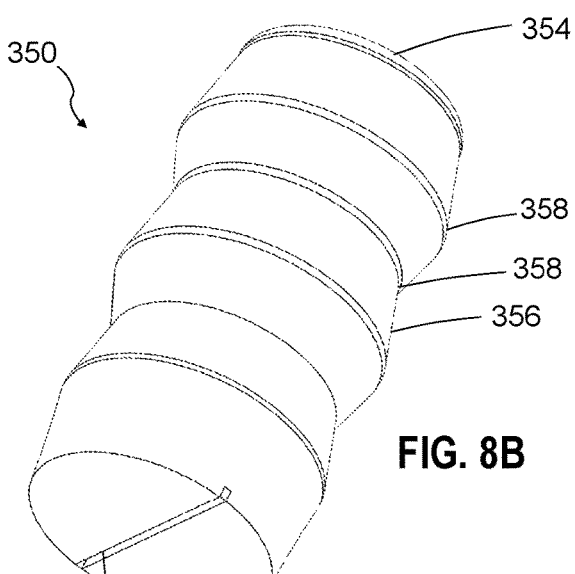

As shown in FIGS. 8A and 8B, the proximal surface 352 includes a slit 362 in fluid communication with a fluid reservoir 360, the fluid reservoir being defined by a cavity within the elongated cylindrical body 356 extending from the proximal surface 352 to the distal surface 354. The slit 362 is disposed on the proximal surface 352. The distal surface 354 of the corrugated capsule 350 abuts the top wall 114 of the cavity 130 of the housing 110. In an initial, uncompressed state, the slit 362 is fluidly closed, the fluid reservoir 360 retaining disinfectant due to negative pressure within the fluid reservoir 360. In a final, compressed state, upon compression of the elongated cylindrical body 356 due to insertion of the hub of the luer connector, the at least one corrugation 358 collapses on one another causing a pressure buildup within the reservoir 360. The buildup of pressure causes the slit 362 to deform and open, causing disinfectant to eject from the slit 362, disinfecting the hub and the periphery of the luer connector.

Figure 8C:
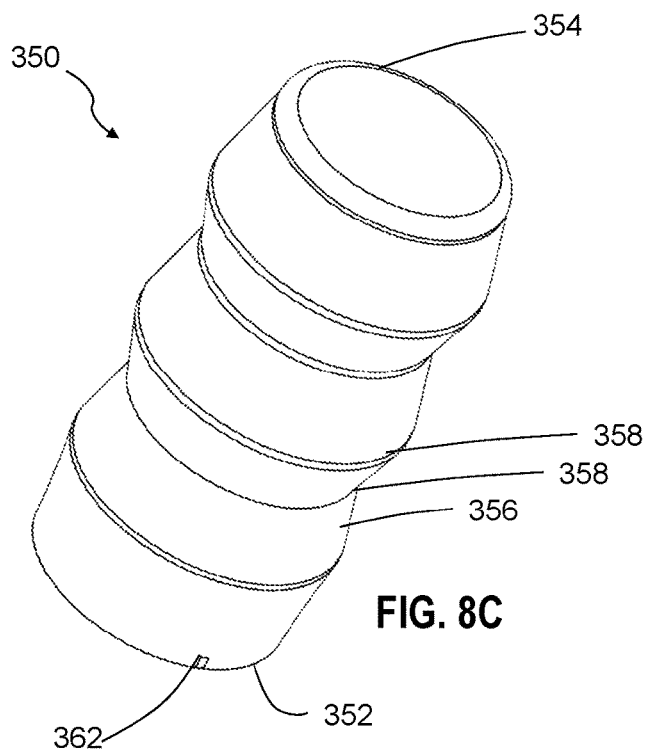

As shown in FIG. 8C, the distal surface 354 has a closed end. In one or more embodiments, the closed end of the distal surface 354 is chamfered. In one or more embodiments, the closed end of the distal surface 354 is rounded.

Figure 9A:
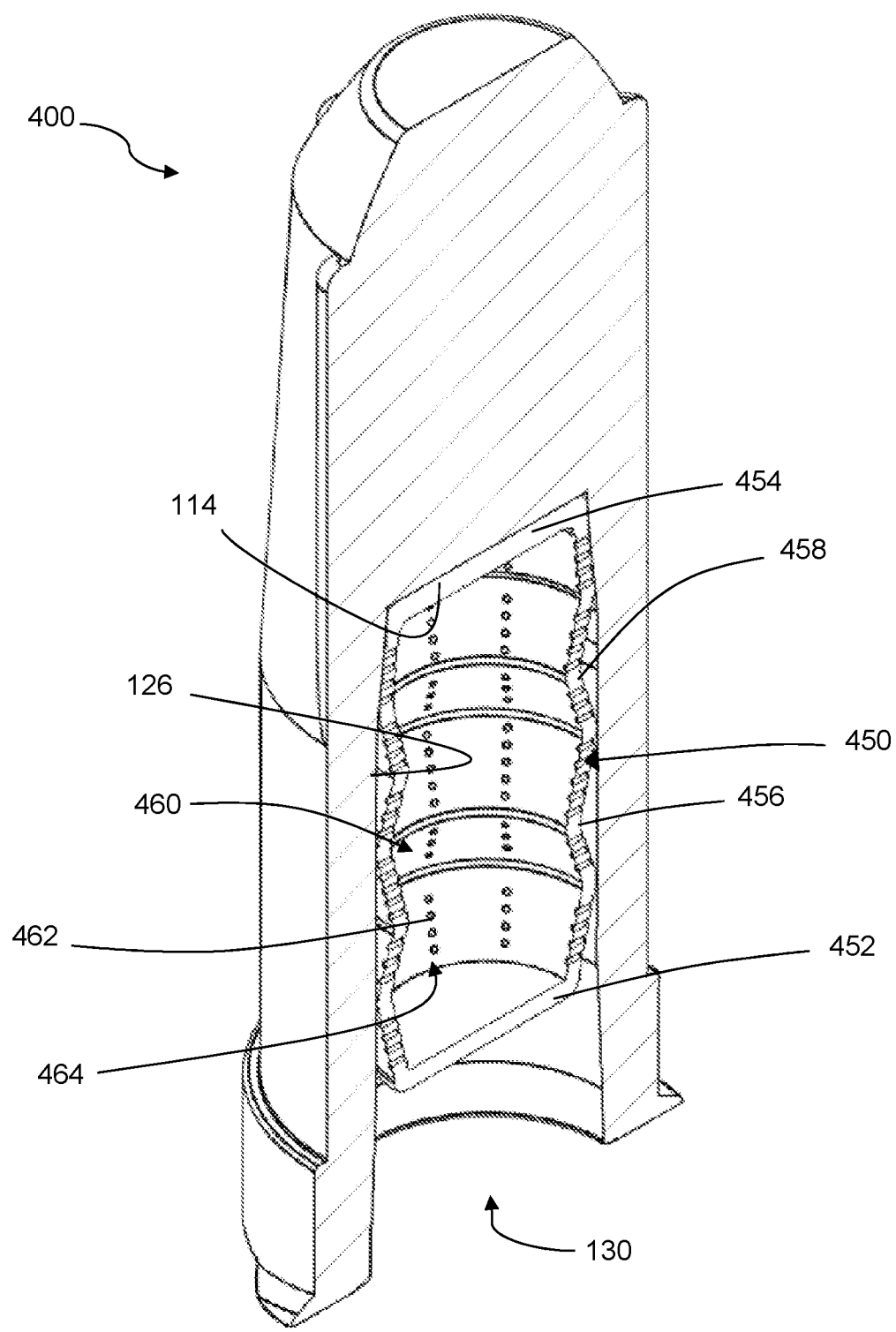
FIG. 9A illustrates a side perspective cross-sectional view of a disinfectant cap and a corrugated capsule disposed within, according to an exemplary fourth embodiment of the present disclosure.
Figure 9B:
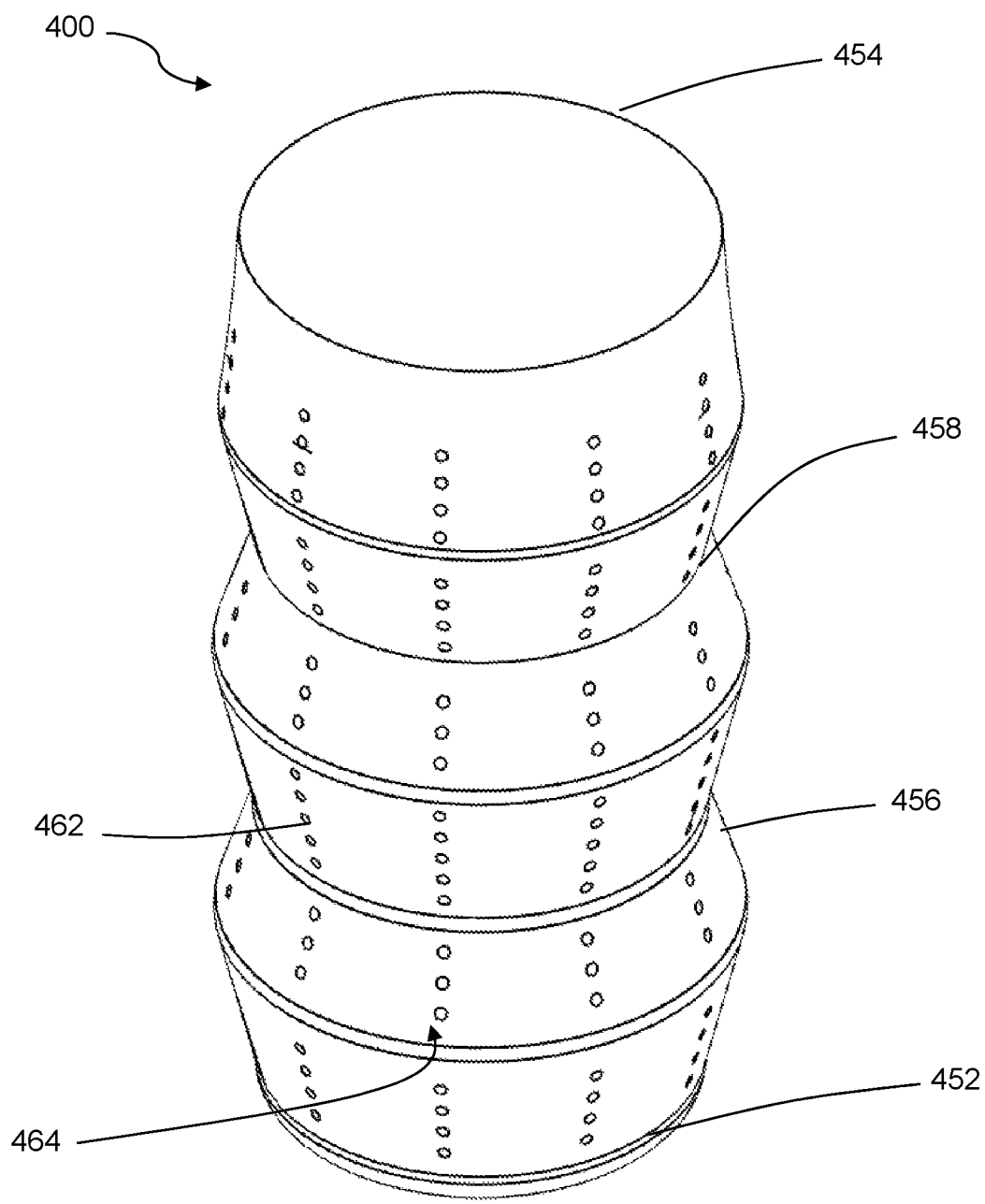
FIG. 9B illustrates a perspective view of the corrugated capsule of the disinfection cap of FIG. 9A.

In accordance with a fourth embodiment of the present disclosure, and as shown in FIGS. 9A and 9B, an exemplary corrugated capsule 450 is disclosed. The corrugated capsule 450 of the fourth embodiment of a disinfection cap 400 is disposed within the cavity 130 of the housing 110. The corrugated capsule 450 comprises a proximal surface 452, a distal surface 454, an elongated cylindrical body 456 extending from the proximal surface 452 and the distal surface 454. The distal surface 454 abuts the top wall 114 of the housing 110. The elongated body 456 includes at least one corrugation 458 configured to collapse on one another upon application of pressure on the proximal surface 452 due to insertion of a luer connector hub into the cavity 130 of the housing 120. The elongated body 456 has a height from the proximal surface 452 to the distal surface 454, the height being equal to or slightly less than a height of the cavity 130. In one or more embodiments, the proximal surface 452 and the distal surface 454 have an equal diameter. In one or more embodiments, the diameter of the proximal surface 452 is smaller than the diameter of the distal surface 454.

As shown in FIGS. 9A and 9B, the elongated cylindrical body 456 includes a plurality of perforations 462 in fluid communication with a fluid reservoir 460, the fluid reservoir being defined by a cavity within the elongated cylindrical body 456 extending from the proximal surface 452 to the distal surface 454. In an uncompressed state, the distal surface 454 of the corrugated capsule 450 abuts the top wall 114 of the cavity 130 of the housing 110. In the uncompressed state, the plurality of perforations 462 is configured to not excrete fluid. Upon compression of the elongated cylindrical body 456, the at least one corrugation 458 collapses on one another causing a pressure buildup within the reservoir 460. The buildup of pressure causes disinfectant to excrete through the plurality of perforations 462, disinfecting the hub and the periphery of the luer connector. The plurality of perforations 462 are arranged in at least one row 464 of perforations, the at least one row being disposed longitudinally on the least one corrugation 458. Due to the proximal surface 452 of the corrugated capsule 450 being closed, the lumen of the hub of the luer connector is fluidly blocked from disinfectant ingress into the lumen. In one or more embodiments, the plurality of perforations 462 are arranged in two or more rows 464 of perforations, the two or more rows being disposed longitudinally on the least one corrugation 458. In one or more embodiments, the plurality of perforations 462 is composed of a self-sealing material.

Figure 10:
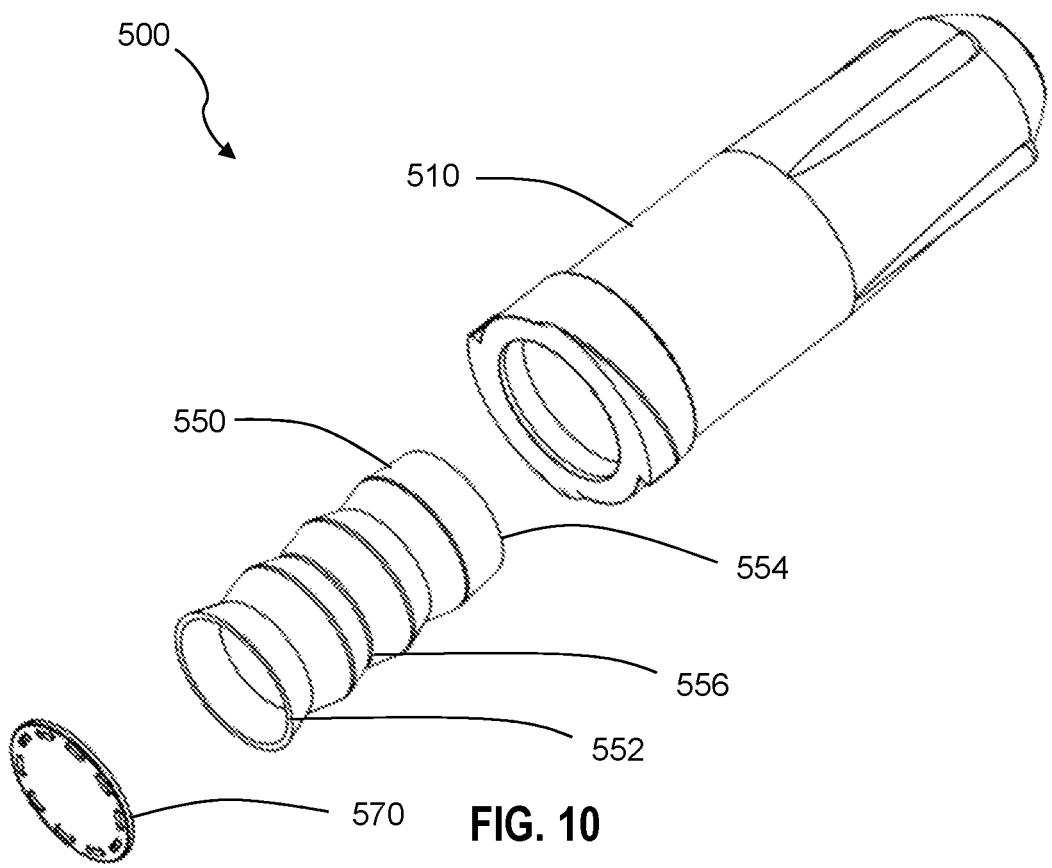
FIG. 10 illustrates an exploded view of a disinfectant cap, and a corrugated capsule and end cap disposed within, according to an exemplary fifth embodiment of the present disclosure.

In accordance with a fifth embodiment of a disinfection cap 500 of the present disclosure, and as shown in FIGS. 10, 11A through 11D, and 12, an exemplary corrugated capsule 550 is disclosed. The corrugated capsule 550 of the third embodiment is disposed within the cavity 130 of the housing 110. As shown in FIG. 10, the corrugated capsule 550 includes an end cap 570 disposed on a proximal surface 552 of the corrugated capsule 550. The corrugated capsule 550 comprises the proximal surface 552, a distal surface 554, an elongated cylindrical body 556 extending from the proximal surface 552 and the distal surface 554. The distal surface 554 abuts the top wall 114 of the housing 110. The elongated body 556 includes at least one corrugation 558 configured to collapse on one another upon application of pressure on the proximal surface 552 due to insertion of a luer connector hub into the cavity 130 of the housing 120. The elongated body 556 has a height from the proximal surface 552 to the distal surface 554, the height being equal to or slightly less than a height of the cavity 130. In one or more embodiments, the proximal surface 552 and the distal surface 554 have an equal diameter. In one or more embodiments, the diameter of the proximal surface 552 is smaller than the diameter of the distal surface 554. The elongated cylindrical body 556 includes a fluid reservoir 560, the fluid reservoir being defined by a cavity within the elongated cylindrical body 556 extending from the proximal surface 552 to the distal surface 554.

Figure 11A:
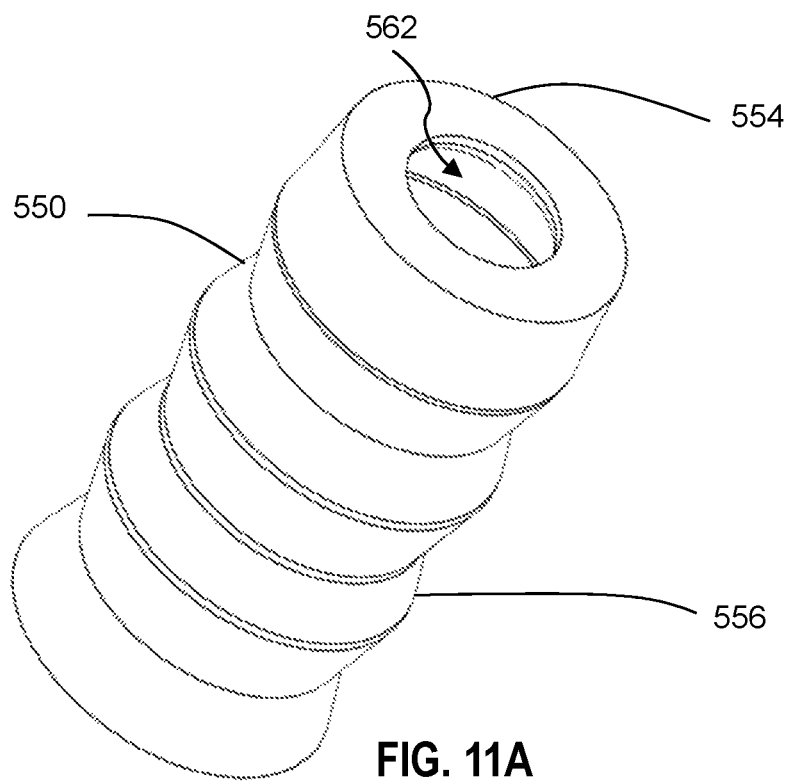
Figure 12:
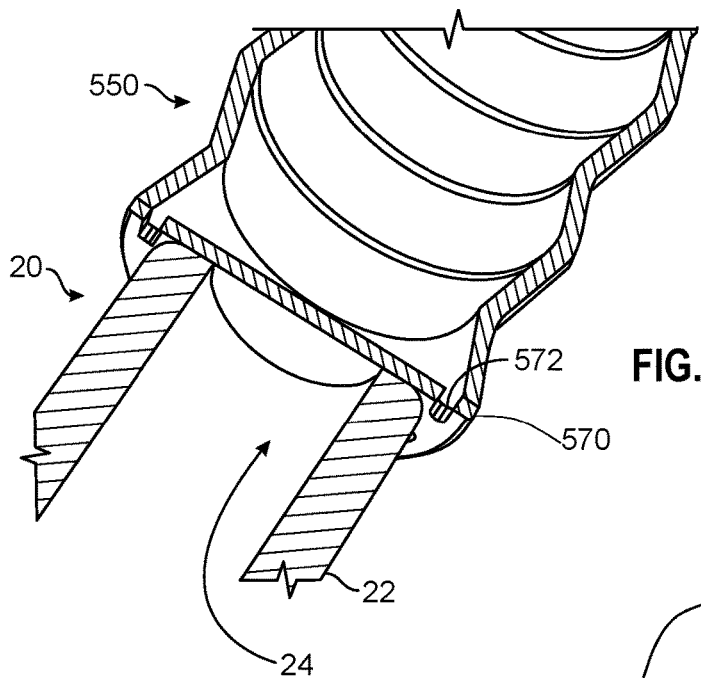
FIG. 12 illustrates a cross-sectional view of the corrugated capsule and end cap abutting a hub of a luer connector, in accordance with the fifth embodiment of FIG. 10.

As shown in FIG. 11A, the distal surface 554 of the corrugated capsule 550 has an aperture 562 extending through the distal surface 554. As shown in FIGS. 11B and 11C, the proximal surface 552 of the corrugated capsule 550 is open, the proximal surface 552 having an engagement surface which abuts the end cap 570. As shown in FIGS. 11C and 11D, the end cap 570 has a cylindrical body comprising a plurality of apertures 572, the plurality of apertures 572 configured to be disposed around a periphery of the end cap 570. As illustrated in a cross-sectional view of FIG. 12, the plurality of apertures 572 are positioned a distance away from a center of the end cap 570 as to not direct fluid flow into the lumen 24 of the hub 22 of the luer connector 20. Thus, upon ejection of disinfectant, ingress into the lumen 24 is prevented.

In an initial, uncompressed state, the distal surface 554 of the corrugated capsule 550 abuts the top wall 114 of the cavity 130 of the housing 110. In a final, compressed state, upon compression of the elongated cylindrical body 556, the at least one corrugation 558 collapses on one another causing a pressure buildup within the reservoir 560. In the uncompressed state, the plurality of apertures 572 are configured to not excrete disinfectant due to negative pressure within the fluid reservoir 560. In a final, compressed state, the buildup of pressure causes disinfectant to excrete through the plurality of apertures 572, disinfecting the hub and the periphery of the luer connector.

As shown in FIGS. 13A through 13C, 14A and 14B, a sixth embodiment of the present disclosure relates to a disinfection cap 600 including a housing 610, the housing 610 having a distal portion 610A and a proximal portion 610B. In one or more embodiments, the proximal portion 610B is substantially cylindrical having a cylindrical housing 610. In one or more embodiments, the distal portion 610A of the housing has a dual winged protrusion 613 for gripping the cap 600. In one or more embodiments, the distal portion 610A and proximal portion 610B have a substantially cylindrical sidewall. In one or more embodiments, an inner surface 626 of the proximal portion 610B of the housing 610 defines a cavity 630 having open bottom 616 for receiving a hub of a luer connector. In one embodiment, distal portion 610A is integrally formed with the proximal portion 610B. In one or more alternate embodiments, distal portion 610A and proximal portion 610B are non-removably or removably assembled with a threaded connection, press-fit connection, adhesive connection or a combination thereof.

In one or more embodiments, the cavity 630 can be configured to facilitate a loose fit between the cavity 630 and the hub of the luer connector, wherein the disinfection cap 500 is secured by an at least one thread 622 or set of tabs included on the outer surface of the housing 610. The at least one thread 622 disposed on the outer surface of the housing 610 is sized and have a thread pattern that will engage with a standard ISO-2 type fitting. The loose fit allows for fluid to flow around the hub of the luer connector. In further embodiments, the cavity 630 is configured in a Luer Slip fitting to facilitate an interference fit between the cavity 630 and the hub of the luer connector. In some embodiments, the interference fit can be configured to be sufficiently strong enough to not require a threaded connection or the at least one thread 622 in removably securing the cavity 630 to the luer connector.

In one or more embodiments, when the hub of the luer connector is received within the inner surface 626 of the cavity 630, the hub is secured within the cavity 630 of the disinfection cap 600 by interlocking at least a portion of the at least one thread 622 with a mating feature on the hub of the luer connector. In one or more embodiments, the at least one thread 622 can include an inclined thread pattern. In one or more embodiments, the at least one thread 622 can include a helical-shaped thread pattern. Such connectors are generally and commonly used as catheter and other fluid-tight protective connectors in medical applications. In some embodiments, the disinfection cap 600 provides a protective cover for a luer connector when engaged with the connector when threads from the luer connector engage and form a releasable connection with at least one thread 622 of disinfection cap 600.

Figure 13A:
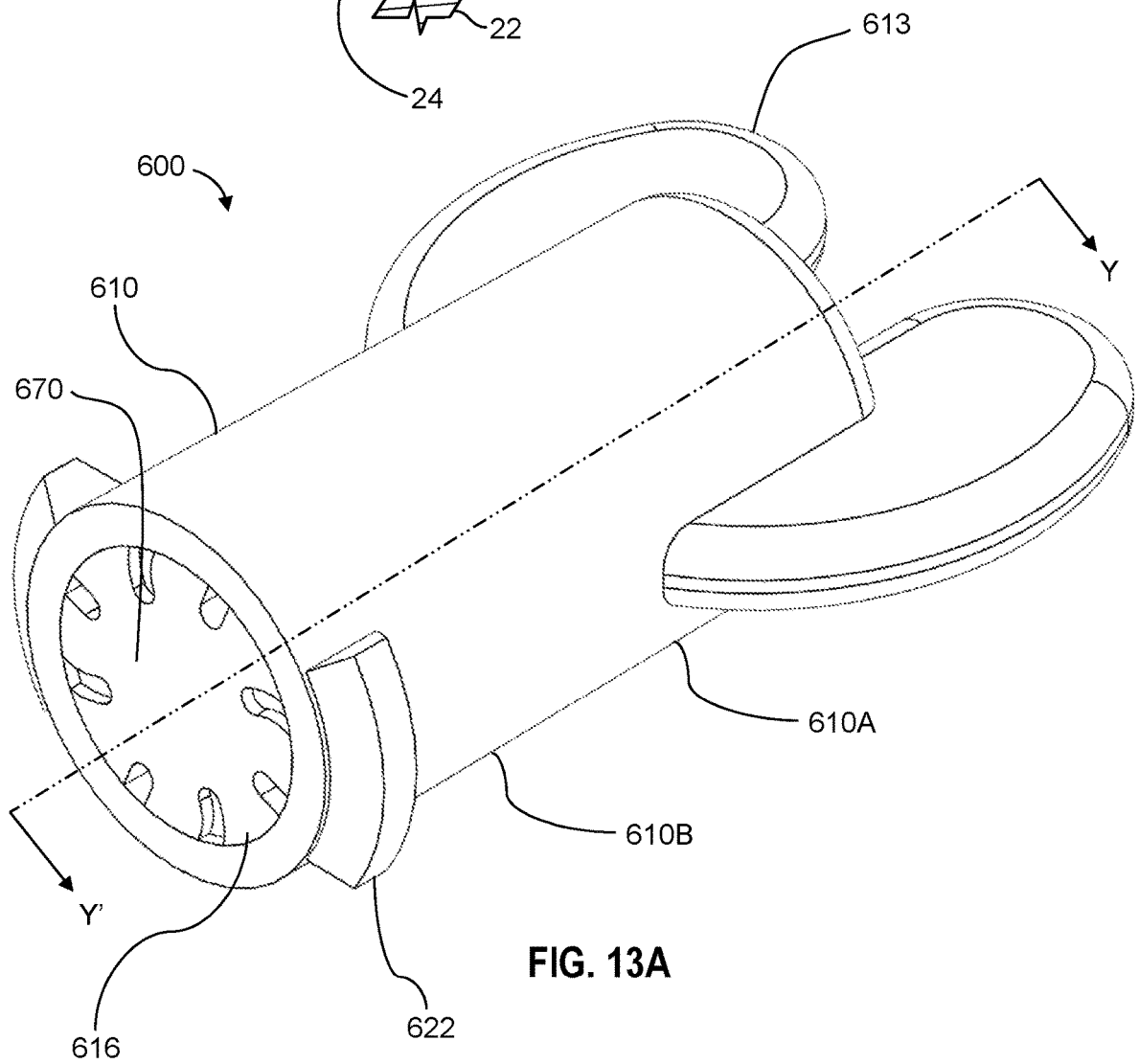
FIG. 13A illustrates a perspective view of a disinfectant cap according to an exemplary sixth embodiment of the present disclosure.
Figure 13B:
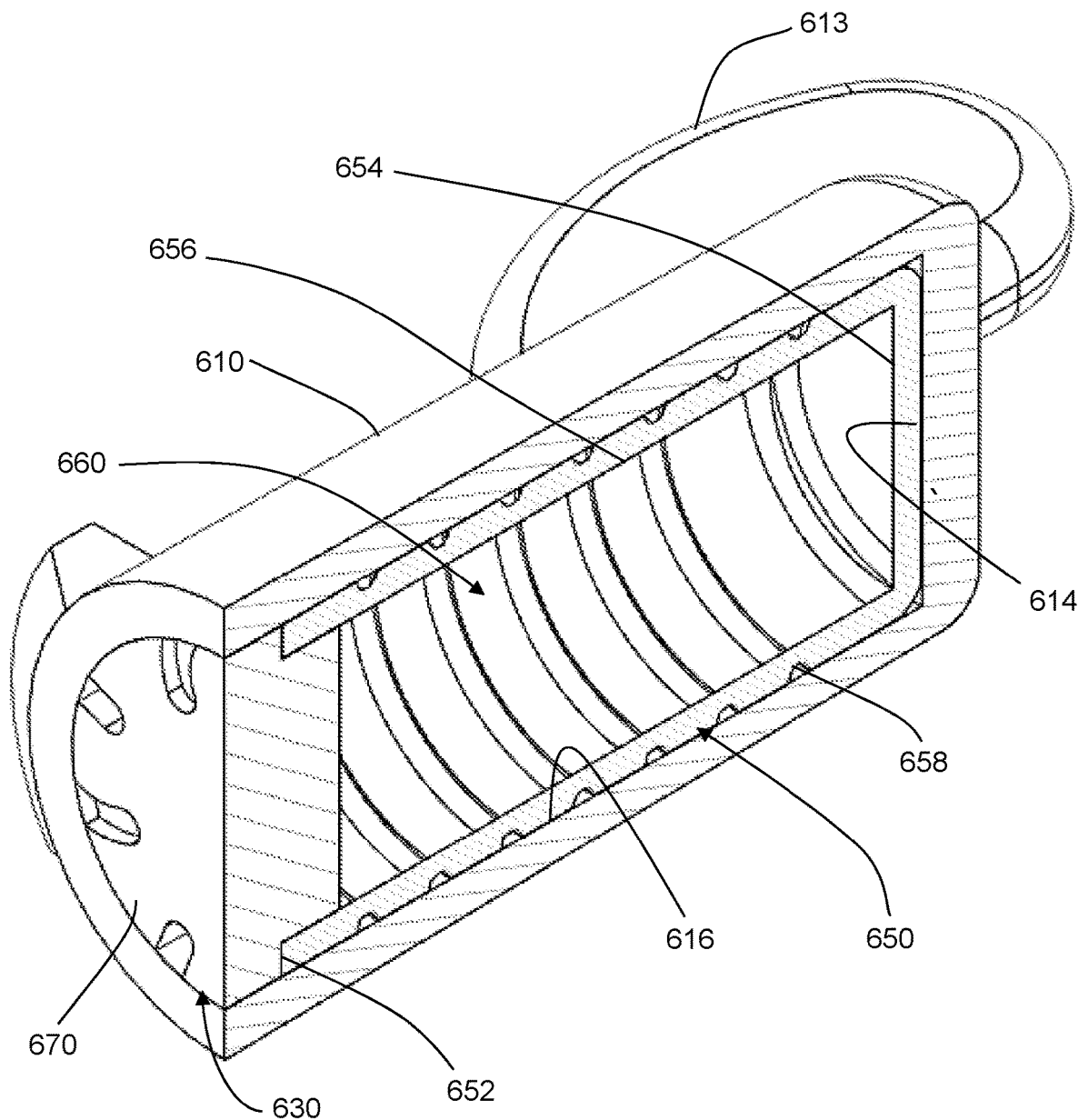
FIG. 13B illustrates a cross-sectional view of the disinfectant cap in accordance with the sixth embodiment of FIG. 13A.
Figure 13C:
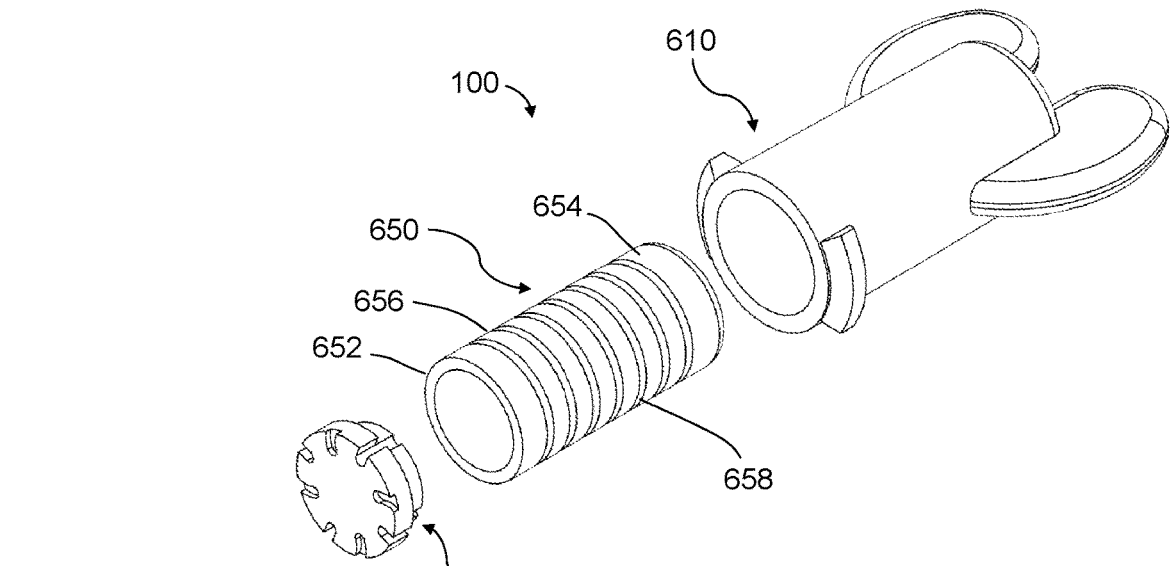
FIG. 13C illustrates an exploded view of the disinfectant cap in accordance with the sixth embodiment of FIG. 13A.

FIG. 13B depicts a cross-sectional view of the disinfection cap 600 along a Y-Y' plane as shown in FIG. 13A. FIG. 13C depicts an exploded view of the disinfection cap 600, the disinfection cap 600 having a corrugated capsule 650 disposed within the cavity 630. The corrugated capsule 650 comprises a closed distal end 654 and an open proximal end 652 defining a fluid reservoir 660. Between the closed distal end 654 and the open proximal end 652 is an elongated cylindrical body 656. Disposed against the open proximal end 652 is a piston 670. As depicted in FIGS. 13B and 13C, a total length of the corrugated capsule 650 and the piston 670 is equal to or less than a length of the cavity 630 of the housing 612.

Figure 14A:
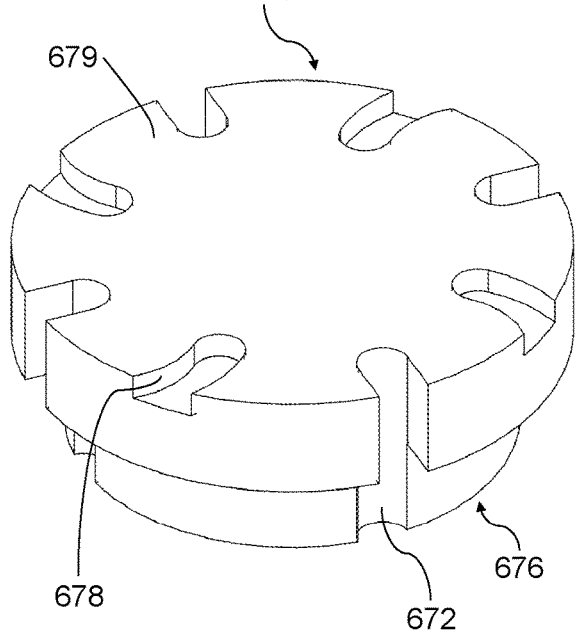
FIGS. 14A and 14B illustrate perspective views of a piston of the disinfection cap of FIG. 13A.
Figure 14B:
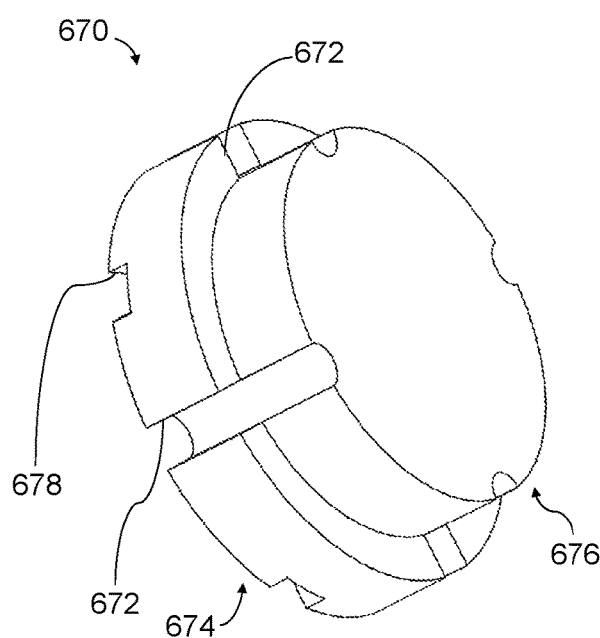

As shown in FIGS. 14A and 14B, the piston 670 comprises a proximal portion 674 and a distal portion 676. The proximal portion 674 has a diameter equal to or slightly less than a diameter of the corrugated capsule 650. The distal portion 676 has a diameter less than the proximal portion 674. The diameter of the distal portion 676 is less than or equal to a diameter of the fluid reservoir 660 such that the distal portion 676 is positioned within the fluid reservoir 660, creating a liquid tight seal. The piston 670 further includes a plurality of apertures 672 extending from the distal portion 676 of the corrugated capsule 650 to the proximal portion 674 of the corrugated capsule 650. The plurality of apertures 672 are in fluid communication with the fluid reservoir 660 and are configured to eject disinfectant upon compression of the corrugated capsule 650. The piston further includes a plurality of directional channels 678 disposed on a proximal surface 679 of the proximal portion 674 of the piston 670. The plurality of directional channels 678 are configured to direct disinfectant towards the periphery of the luer hub of the luer connector. The plurality of directional channels 678 are configured to be disposed around a periphery of the proximal surface 679 of the piston 670. The plurality of directional channels 678 are positioned a distance away from a center of the proximal surface 679 as to not direct fluid flow into the lumen of the hub of the luer connector. Thus, upon ejection of disinfectant, ingress into the lumen is prevented.

As previously described, and as illustrated in FIGS. 15A and 15B, the diameter of the proximal portion 674 of the piston 670 is equal to or slightly less than the diameter of the corrugated capsule 650. The diameter of the distal portion 676 of the piston 670 is less than the proximal portion 674. The diameter of the distal portion 676 is less than or equal to a diameter of the fluid reservoir 660 such that the distal portion 676 is positioned within the fluid reservoir 660, creating a liquid tight seal. The elongated cylindrical body 656 has at least one corrugation 658 along the elongated cylindrical body 656. In one or more embodiments, the at least one corrugation 658 defines a cross-section of the elongated cylindrical body 646 having a sidewall thickness which is less than a sidewall thickness of the elongated cylindrical body 656.

In an uncompressed state, the distal end 654 of the corrugated capsule 650 abuts the top wall 614 of the cavity 630 of the housing 610. Upon compression of the elongated cylindrical body 656, the at least one corrugation 658 collapses on one another causing a pressure buildup within the reservoir 660. In the uncompressed state, the plurality of apertures 672 are configured to not excrete fluid due to negative pressure within the fluid reservoir 660. The buildup of pressure causes disinfectant to excrete through the plurality of apertures 662, disinfecting the hub and the periphery of the luer connector.

The corrugated capsule (350, 450, 550, 650) is of a flexible elastomer material. The disinfection cap (100, 200, 300, 400, 500 600) is made from any of a number of types of plastic materials such as polycarbonate, polypropylene, polyethylene, polyethylene terephthalate, polylactide, TPU, TPE, PVC, LSR, EPDM, Viton, acrylonitrile butadiene styrene or any other moldable plastic material used in medical devices. In one or more embodiments, the disinfection cap (100, 200, 300, 400, 500, 600) comprises a polypropylene or polyethylene material.

In one or more embodiments, the disinfectant is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

In one or more embodiments, the disinfection cap (100, 200, 300, 400, 500, 600) can include a removable peel seal covering the opening to the cavity (130, 630). In one or more embodiments, the peelable seal comprises an aluminum or multi-layer polymer film peel back top. In a specific embodiment, the peelable is heat-sealed or induction sealed to the open end of the disinfection cap (100, 200, 300, 400, 500, 600). In one or more embodiments, the peelable seal comprises a moisture barrier.

In one or more embodiments, the connector of the medical device may be selected from the group consisting essentially of needle-free connectors, catheter luer connectors, stopcocks, and hemodialysis connectors on primary IV gravity sets, secondary IV gravity sets, extension sets, and infusion or syringe pump sets. In some embodiments, the disinfection cap can be connected with any of a variety of different needleless injection sites. In one or more embodiments, after the disinfection cap has been coupled with connector, it is unnecessary to disinfect (e.g., treat with an alcohol swab) the connector prior to each reconnection of the connector with another connector, as the connector will be kept in an uncontaminated state while coupled with the disinfection cap. Use of the disinfection cap (100, 200, 300, 400, 500, 600) replaces the standard swabbing protocol for cleaning connectors.

Yet another aspect of the present disclosure pertains to a method of disinfecting a medical connector. The method comprises connecting the disinfection cap (100, 600) of one or more embodiments to a medical connector, wherein connecting includes engaging the threads of the medical connector onto the threads on the outer surface of the sidewall of the housing (110, 610) of the disinfection cap upon insertion of the medical connector into the disinfection cap (100, 200, 300, 400, 500, 600) such that the medical connector compresses the contacts the corrugated capsule (350, 450, 550, 650).

It is contemplated that the disinfection cap (100, 200, 300, 400, 500, 600) disclosed herein and shown in the Figures may also be utilized with luer connectors, including female and male luer connectors, wherein the blockage feature can be used to block the lumen of open luers to facilitate the mitigation of such disinfectant ingress into connectors, thereby reducing risk of the disinfectant entering the blood stream. It is therefore contemplated that the disinfection cap (100, 200, 300, 400, 500, 600) disclosed herein and shown in the Figures may be utilized with male and female luer connectors.

While the present disclosure has been shown and described with reference to certain exemplary embodiments thereof, it will be understood by those skilled in the art that various changes in form and details may be made therein without departing from the spirit and scope of the embodiments of the present disclosure. Also, the inner and/or the outer housing of the disinfection cap can be single shot molded, or made by other suitable process. Furthermore, any of the features or elements of any exemplary implementations of the embodiments of the present disclosure as described above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to be limiting.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A disinfection cap having a housing comprising:
a cylindrical sidewall having an inner surface defining a cavity and a top wall,
an open bottom formed by the cylindrical sidewall with an opening to the cavity within said housing for receiving a hub of a luer connector;
a retention rod disposed within the cavity, the retention rod having a proximal flange, a distal flange and an elongated rod between the proximal flange and distal flange, the distal flange of the retention rod abutting the top wall of the cavity, wherein a diameter of the proximal flange of the retention rod is equal to or slightly larger than a diameter of a proximal portion of the cavity, configured to have an interference fit sufficient to create a fluid seal between the proximal flange of the retention rod and the proximal portion of the cavity;
a fluid reservoir defined between the inner surface of the housing, the proximal flange of the retention rod and the distal flange of the retention rod; and,
a disinfectant disposed within the fluid reservoir, the disinfectant being retained within the fluid reservoir in an initial state, wherein the hub of said luer connector is received within said inner surface of said cavity.

2. The disinfection cap of claim 1, wherein a diameter of the elongated rod is configured to buckle to a final state upon insertion of a hub of the luer connector when the hub of the luer connector is received within the cavity, thereby breaking the fluid seal between the proximal flange and the proximal portion of the cavity and releasing disinfectant into the cavity disinfecting the hub and a periphery of the luer connector.

3. The disinfection cap of claim 2, wherein at least one circular fin is disposed on the elongated rod, the at least one circular fin having a thickness configured to elastically deform, whereby pressure buildup within the fluid reservoir due to insertion of the luer connector causes deformation of the at least one fin.

4. The disinfection cap of claim 1, wherein a diameter of the elongated rod is configured to compress upon insertion of the hub of the luer connector when the hub of the luer connector is received within the cavity.

5. The disinfection cap of claim 1, wherein a diameter of the distal flange is equal to or larger than a diameter of a distal portion of the cavity configured to create an interference fit sufficient enough to removably hold the retention rod within the cavity.

6. The disinfection cap of claim 1, wherein the disinfection cap is secured by an at least one thread or set of tabs included on an outer surface of the housing.

7. The disinfection cap of claim 6, wherein the at least one thread can include an inclined thread pattern.

8. The disinfection cap of claim 6, wherein the at least one thread can include a helical-shaped thread pattern.

9. The disinfection cap of claim 1, wherein the retention rod has a height from the proximal flange to the distal flange, the height being equal to or slightly less than a height of the cavity.

10. The disinfection cap of claim 1, wherein the distal flange is chemically bonded with adhesive to the top wall of the housing.

11. The disinfection cap of claim 1, wherein the proximal flange conforms to the hub of the luer connector upon insertion of the luer connector.

12. The disinfection cap of claim 1, wherein the elongated rod buckles into a toroid structure, while the proximal flange does not rotate.

13. The disinfection cap of claim 1, wherein compression of the retention rod (150) causes the proximal flange to buckle and rotate.

* * * * *

UNITED STATES PATENT AND TRADEMARK OFFICE
CERTIFICATE OF CORRECTION

| | |
|---|---|
| PATENT NO. | : 12,005,223 B2 |
| APPLICATION NO. | : 17/229166 |
| DATED | : June 11, 2024 |
| INVENTOR(S) | : Chang Jiang et al. |

It is certified that error appears in the above-identified patent and that said Letters Patent is hereby corrected as shown below:

On the Title Page

Page 2, Column 2, Line 25, item [56] replace "1" after "JP" and before "03139363 A" with "H".

Signed and Sealed this
Sixteenth Day of July, 2024

Katherine Kelly Vidal
*Director of the United States Patent and Trademark Office*